(12) United States Patent
Qu et al.

(10) Patent No.: US 11,780,923 B2
(45) Date of Patent: Oct. 10, 2023

(54) PD-L1 ANTIBODY, ANTIGEN-BINDING FRAGMENT THEREOF AND MEDICAL APPLICATION THEREOF

(71) Applicants: Suzhou Suncadia Biopharmaceuticals Co., Ltd., Jiangsu (CN); Jiangsu Hengrui Medicine Co., Ltd., Jiangsu (CN); Shanghai Hengrui Pharmaceutical Co., Ltd., Shanghai (CN)

(72) Inventors: Xiangdong Qu, Shanghai (CN); Qiyue Hu, Shanghai (CN); Shaoyu Xu, Shanghai (CN); Dongbing Cui, Shanghai (CN); Houcong Jin, Shanghai (CN); Weikang Tao, Shanghai (CN); Lianshan Zhang, Shanghai (CN); Guoqing Cao, Shanghai (CN); Piaoyang Sun, Jiangsu (CN)

(73) Assignees: Suzhou Suncadia Biopharmaceuticals Co., Ltd., Jiangsu (CN); Jiangsu Hengrui Medicine Co., Ltd., Lianyungang (CN); Shanghai Hengrui Pharmaceutical Co., Ltd., Shanghai (CN)

(*) Notice: Subject to any disclaimer, the term of this patent is extended or adjusted under 35 U.S.C. 154(b) by 513 days.

(21) Appl. No.: 16/947,583

(22) Filed: Aug. 7, 2020

(65) Prior Publication Data
US 2020/0399375 A1 Dec. 24, 2020

Related U.S. Application Data

(62) Division of application No. 15/775,598, filed as application No. PCT/CN2016/104320 on Nov. 2, 2016, now Pat. No. 10,815,304.

(30) Foreign Application Priority Data
Nov. 17, 2015 (CN) .......................... 201510788907.3

(51) Int. Cl.
C07K 16/28 (2006.01)
A61K 39/395 (2006.01)
A61P 35/00 (2006.01)
A61K 39/00 (2006.01)

(52) U.S. Cl.
CPC ........ *C07K 16/2827* (2013.01); *A61K 39/395* (2013.01); *A61P 35/00* (2018.01); *C07K 16/28* (2013.01); *A61K 2039/505* (2013.01); *A61K 2039/572* (2013.01); *C07K 2317/24* (2013.01); *C07K 2317/40* (2013.01); *C07K 2317/52* (2013.01); *C07K 2317/56* (2013.01); *C07K 2317/565* (2013.01); *C07K 2317/567* (2013.01); *C07K 2317/732* (2013.01); *C07K 2317/734* (2013.01); *C07K 2317/92* (2013.01)

(58) Field of Classification Search
CPC ........ A61K 39/39558; A61K 2039/505; C07K 16/28; C07K 2317/24; C07K 2317/565
USPC ....................................................... 424/133.1
See application file for complete search history.

(56) References Cited

U.S. PATENT DOCUMENTS

| | | | |
|---|---|---|---|
| 6,803,192 B1 | 10/2004 | Chen | |
| 8,617,546 B2 | 12/2013 | Kang et al. | |
| 9,334,331 B2* | 5/2016 | Igawa | C07K 16/40 |
| 10,421,807 B2* | 9/2019 | Gonzales | A61P 11/00 |
| 11,359,021 B2* | 6/2022 | Gu | C07K 16/2827 |
| 2012/0237522 A1 | 9/2012 | Kang et al. | |
| 2014/0335093 A1 | 11/2014 | Olive | |
| 2020/0069800 A1* | 3/2020 | Yan | A61K 47/12 |
| 2023/0012428 A1* | 1/2023 | Gu | C07K 14/70503 |
| 2023/0203119 A1* | 6/2023 | Baliga | C07K 16/2827 |
| | | | 424/134.1 |

FOREIGN PATENT DOCUMENTS

| | | |
|---|---|---|
| CN | 101104640 A | 1/2008 |
| WO | 0139722 A2 | 6/2001 |
| WO | 2007005874 A3 | 1/2007 |
| WO | 2010089411 A2 | 8/2010 |
| WO | 2011066389 A1 | 6/2011 |
| WO | 2013173223 A1 | 11/2013 |
| WO | 2013181634 A2 | 12/2013 |
| WO | 2014022758 A1 | 2/2014 |
| WO | 2014055897 A2 | 4/2014 |
| WO | 2014100079 A1 | 6/2014 |
| WO | 2014151006 A2 | 9/2014 |
| WO | 2014195852 A1 | 12/2014 |

(Continued)

OTHER PUBLICATIONS

Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*

(Continued)

Primary Examiner — Lynn A Bristol
(74) Attorney, Agent, or Firm — Ice Miller LLP

(57) ABSTRACT

The present invention relates to a PD-L1 antibody, antigen-binding fragments, and medical application thereof. Further, the present invention relates to chimeric antibodies and humanized antibodies comprising the CDR regions of the present PD-L1 antibody, as well as a pharmaceutical composition comprising the present PD-L1 antibody and the antigen-binding fragments thereof, and their use as anti-cancer drugs. In particular, the present invention relates to a humanized PD-L1 antibody and its use in preparation of a medicament for the treatment of PD-L1 mediated disease or disorder.

23 Claims, 2 Drawing Sheets

Specification includes a Sequence Listing.

(56) References Cited

FOREIGN PATENT DOCUMENTS

| WO | 2015036511 A1 | 3/2015 |
|---|---|---|
| WO | 2015048520 A1 | 4/2015 |

OTHER PUBLICATIONS

Thurber et al. (Adv. Drug Deliv. Rev. 60:1421-1434 (2008)).*
Rudnick et al. (Can. Biotherp. & Radiopharm. 24: 155-162 (2009)).*
Huang et al. (Appl Microbiol Biotechnol (2010) 87:401-410).*
Colman, "(Effects of amino acid sequence changes on antibody-antigen interactions," Research in Immunol., vol. 145, No. 1, pp. 33-36 (1994).
MacCallum et al., "Antibody-antigen interactions: contact analysis and binding site topography," J. Mol. Biol. vol. 262, No. 5, pp. 732-745 (1996).
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology, vol. 169, No. 6, pp. 3076-3084 (2002).
Casset et al., "A peptide mimetic of an anti-CD4 monoclonal antibody by rational design," BBRC, vol. 307, Issue 1, pp. 198-205 (2003).
Vajdos et al., "Comprehensive functional maps of the antigen-binding site of an anti-ErbB2 antibody obtained with shotgun scanning mutagenesis," J. Mol. Biol., vol. 320, No. 2, pp. 415-428 (2002).
Holm et al., "Functional Mapping and Single Chain Construction of the Anti-Cytokeratin 8 Monoclonal Antibody TS1," Mol. Innn-nunol., vol. 44, pp. 1075-1084 (2007).
Chen et al., "Selection and analysis of an optimized anti-VEGF antibody: crystal structure of an affinity-matured Fab in complex with antigen," J. Mol. Bio., vol. 293, No. 4, pp. 865-881 (1999).
Wu et al., "Humanization of a murine monoclonal antibody by simultaneous optimization of framework and CDR residues," J. Mol. Biol., vol. 294, No. 1, pp. 151-162 (1999).
Brummell et al., "Probing the combining site of an anti-carbohydrate antibody by saturation-mutagenesis: role of the heavy-chain CDR3 residues," Biochemistry, vol. 32, No. 4, pp. 1180-1187 (1993).
Kobayashi et al., "Tryptophan H33 plays an important role in pyrimidine (6-4) pyrimidone photoproduct binding by a high-affinity antibody," Protein Engineering, vol. 12, Issue 10, pp. 879-844 (1999).
Burks et al., "In vitro scanning saturation mutagenesis of an antibody binding pocket," PNAS, vol. 94, No. 2, pp. 412-417 (1997).
Jang et al., "The structural basis for DNA binding by an anti-DNA autoantibody," Molec. Immunol., vol. 35, No. 18, pp. 1207-1217 (1998).
Brorson et al., "Mutational Analysis of Avidity and Fine Specificity of Anti-Levan Antibodies," J. Immunol., vol. 163, No. 12, pp. 6694-6701 (1999).
Chen et al., "Anti-PD-1/PD-L1 therapy of human cancer: past, present, and future," J Clin Invest., vol. 125, No. 9, pp. 3384-3391 (2015).

* cited by examiner

```
                        SEQUENCE LISTING

<160> NUMBER OF SEQ ID NOS: 41

<210> SEQ ID NO 1
<211> LENGTH: 290
<212> TYPE: PRT
<213> ORGANISM: Homo sapiens

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
```

```
                    50                  55                  60
Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
        130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 2
<211> LENGTH: 242
<212> TYPE: PRT
<213> ORGANISM: Artificial sequence
<220> FEATURE:
<223> OTHER INFORMATION: Immunogen:PD-L1 with His, PADRE tag:PD-L1(ECD)-
      PADRE-His6

<400> SEQUENCE: 2

Phe Thr Val Thr Val Pro Lys Asp Leu Tyr Val Val Glu Tyr Gly Ser
 1               5                  10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Arg Cys
                 85                  90                  95

Met Ile Ser Tyr Gly Gly Ala Asp Tyr Lys Arg Ile Thr Val Lys Val
            100                 105                 110
```

-continued

```
Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Arg Leu Asp Pro Glu Glu Asn His Thr Ala Glu Leu Val Ile
            195                 200                 205

Pro Glu Leu Pro Leu Ala His Pro Pro Asn Glu Arg Gly Ser Gly Ala
210                 215                 220

Lys Phe Val Ala Ala Trp Thr Leu Lys Ala Ala Ala His His His His
225                 230                 235                 240

His His
```

<210> SEQ ID NO 3
<211> LENGTH: 234
<212> TYPE: PRT
<213> ORGANISM: Artificial sequence
<220> FEATURE:
<223> OTHER INFORMATION: PD-L1 with FLAG and HIS tag(ECD immunogen):PD-L1(ECD)-Flag-His6

<400> SEQUENCE: 3

```
Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
        50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Arg Leu Asp Pro Glu Glu Asn His Thr Ala Glu Leu Val Ile
            195                 200                 205

Pro Glu Leu Pro Leu Ala His Pro Pro Asn Glu Arg Asp Tyr Lys Asp
210                 215                 220
```

Asp Asp Asp Lys His His His His His His
225                 230

<210> SEQ ID NO 4
<211> LENGTH: 447
<212> TYPE: PRT
<213> ORGANISM: Artificial sequence
<220> FEATURE:
<223> OTHER INFORMATION: PD-L1 Fc fusion protein:PD-L1(ECD)-Fc

<400> SEQUENCE: 4

Phe Thr Val Thr Val Pro Lys Asp Leu Tyr Val Val Glu Tyr Gly Ser
1               5                   10                  15

Asn Met Thr Ile Glu Cys Lys Phe Pro Val Lys Gln Leu Asp Leu
            20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
        50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

```
Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 5
<211> LENGTH: 382
<212> TYPE: PRT
<213> ORGANISM: Artificial sequence
<220> FEATURE:
<223> OTHER INFORMATION: PD-1 Fc fusion protein:PD-1(ECD)-Fc

<400> SEQUENCE: 5

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Glu Pro Lys Ser Ser Asp Lys Thr His Thr
145                 150                 155                 160

Cys Pro Pro Cys Pro Ala Pro Glu Leu Leu Gly Gly Pro Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser His Glu Asp Pro Glu Val
        195                 200                 205

Lys Phe Asn Trp Tyr Val Asp Gly Val Glu Val His Asn Ala Lys Thr
    210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
            260                 265                 270
```

```
Lys Ala Lys Gly Gln Pro Arg Glu Pro Gln Val Tyr Thr Leu Pro Pro
            275                 280                 285

Ser Arg Asp Glu Leu Thr Lys Asn Gln Val Ser Leu Thr Cys Leu Val
    290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Val Leu Asp Ser Asp
                325                 330                 335

Gly Ser Phe Phe Leu Tyr Ser Lys Leu Thr Val Asp Lys Ser Arg Trp
            340                 345                 350

Gln Gln Gly Asn Val Phe Ser Cys Ser Val Met His Glu Ala Leu His
        355                 360                 365

Asn His Tyr Thr Gln Lys Ser Leu Ser Leu Ser Pro Gly Lys
    370                 375                 380

<210> SEQ ID NO 6
<211> LENGTH: 118
<212> TYPE: PRT
<213> ORGANISM: Artificial sequence
<220> FEATURE:
<223> OTHER INFORMATION: Murine 9-2 VH

<400> SEQUENCE: 6

Glu Val Gln Leu Gln Glu Ser Gly Pro Gly Leu Ala Lys Pro Ser Gln
1               5                   10                  15

Thr Leu Ser Leu Thr Cys Ser Val Ala Gly Tyr Ser Ile Thr Asn Asp
            20                  25                  30

Tyr Trp Asn Trp Ile Arg Lys Phe Pro Gly Asn Lys Leu Glu Tyr Met
        35                  40                  45

Gly Tyr Ile Ser Tyr Thr Gly Ser Thr Tyr Tyr Asn Pro Ser Leu Lys
    50                  55                  60

Ser Arg Leu Ser Ile Thr Arg Asp Thr Ser Lys Asn Gln Tyr Tyr Leu
65                  70                  75                  80

Gln Leu Asn Ser Val Thr Ala Glu Asp Thr Ala Ile Tyr Tyr Cys Ala
                85                  90                  95

Arg Ser Gly Gly Trp Leu Ala Pro Phe Asp Tyr Trp Gly Arg Gly Thr
            100                 105                 110

Thr Leu Thr Val Ser Ser
        115

<210> SEQ ID NO 7
<211> LENGTH: 113
<212> TYPE: PRT
<213> ORGANISM: Artificial sequence
<220> FEATURE:
<223> OTHER INFORMATION: Murine 9-2 VL

<400> SEQUENCE: 7

Asp Ile Val Met Ser Gln Ser Pro Ser Ser Leu Val Val Ser Val Gly
1               5                   10                  15

Glu Lys Val Ile Met Ser Cys Lys Ser Ser Gln Ser Leu Phe Tyr Arg
            20                  25                  30

Ser Asn Gln Lys Asn Ser Leu Ala Trp Tyr Gln Gln Lys Pro Gly Gln
        35                  40                  45

Ser Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Val Thr
65                  70                  75                  80
```

```
Ile Ser Ser Val Lys Ala Glu Asp Leu Ala Val Tyr Tyr Cys Gln Gln
                85                  90                  95

Tyr Tyr Gly Tyr Pro Tyr Thr Phe Gly Gly Gly Thr Lys Leu Glu Ile
            100                 105                 110

Lys

<210> SEQ ID NO 8
<211> LENGTH: 119
<212> TYPE: PRT
<213> ORGANISM: Artificial sequence
<220> FEATURE:
<223> OTHER INFORMATION: Murine 24D5 VH

<400> SEQUENCE: 8

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Gln Gln Arg Pro Gly Gln Gly Leu Glu Trp Ile
            35                  40                  45

Gly Arg Ile His Pro Asn Ser Gly Gly Thr Ser Tyr Asn Glu Lys Phe
    50                  55                  60

Lys Asn Arg Ala Thr Leu Thr Val Asp Lys Ser Ser Ser Thr Ala Tyr
65                  70                  75                  80

Met Gln Phe Ser Ser Leu Thr Ser Glu Asp Ser Ala Val Tyr Tyr Ser
                85                  90                  95

Ala Arg Gly Gly Ser Ser Tyr Asp Tyr Phe Asp Tyr Trp Gly Gln Gly
            100                 105                 110

Thr Thr Leu Thr Val Ser Ser
        115

<210> SEQ ID NO 9
<211> LENGTH: 111
<212> TYPE: PRT
<213> ORGANISM: Artificial sequence
<220> FEATURE:
<223> OTHER INFORMATION: Murine 24D5 VL

<400> SEQUENCE: 9

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Ser Ile His
                20                  25                  30

Gly Thr His Leu Met His Trp Tyr Gln Gln Lys Pro Gly Gln Pro Pro
            35                  40                  45

Lys Leu Leu Ile Tyr Ala Ala Ser Asn Leu Glu Ser Gly Val Pro Ala
    50                  55                  60

Arg Phe Ser Gly Ser Gly Ser Glu Thr Asp Phe Thr Leu Asn Ile His
65                  70                  75                  80

Pro Val Glu Glu Glu Asp Ala Thr Thr Tyr Phe Cys Gln Gln Ser Phe
                85                  90                  95

Glu Asp Pro Leu Thr Phe Gly Ala Gly Thr Lys Leu Glu Leu Lys
            100                 105                 110

<210> SEQ ID NO 10
<211> LENGTH: 5
<212> TYPE: PRT
<213> ORGANISM: Artificial sequence
```

```
<220> FEATURE:
<223> OTHER INFORMATION: HCDR1
<220> FEATURE:
<221> NAME/KEY: MISC_FEATURE
<222> LOCATION: (5)..(5)
<223> OTHER INFORMATION: Xaa is from N or T.

<400> SEQUENCE: 10

Asn Asp Tyr Trp Xaa
1               5

<210> SEQ ID NO 11
<211> LENGTH: 16
<212> TYPE: PRT
<213> ORGANISM: Artificial sequence
<220> FEATURE:
<223> OTHER INFORMATION: Murine 9-2 HCDR2

<400> SEQUENCE: 11

Tyr Ile Ser Tyr Thr Gly Ser Thr Tyr Asn Pro Ser Leu Lys Ser
1               5                   10                  15

<210> SEQ ID NO 12
<211> LENGTH: 10
<212> TYPE: PRT
<213> ORGANISM: Artificial sequence
<220> FEATURE:
<223> OTHER INFORMATION: Murine 9-2 HCDR3

<400> SEQUENCE: 12

Ser Gly Gly Trp Leu Ala Pro Phe Asp Tyr
1               5                   10

<210> SEQ ID NO 13
<211> LENGTH: 17
<212> TYPE: PRT
<213> ORGANISM: Artificial sequence
<220> FEATURE:
<223> OTHER INFORMATION: LCDR1
<220> FEATURE:
<221> NAME/KEY: MISC_FEATURE
<222> LOCATION: (9)..(9)
<223> OTHER INFORMATION: Xaa is selected from R or H
<220> FEATURE:
<221> NAME/KEY: MISC_FEATURE
<222> LOCATION: (14)..(14)
<223> OTHER INFORMATION: Xaa is selected from N or H

<400> SEQUENCE: 13

Lys Ser Ser Gln Ser Leu Phe Tyr Xaa Ser Asn Gln Lys Xaa Ser Leu
1               5                   10                  15

Ala

<210> SEQ ID NO 14
<211> LENGTH: 7
<212> TYPE: PRT
<213> ORGANISM: Artificial sequence
<220> FEATURE:
<223> OTHER INFORMATION: Murine 9-2 LCDR2

<400> SEQUENCE: 14

Gly Ala Ser Thr Arg Glu Ser
1               5

<210> SEQ ID NO 15
<211> LENGTH: 9
<212> TYPE: PRT
<213> ORGANISM: Artificial sequence
```

```
<220> FEATURE:
<223> OTHER INFORMATION: Murine 9-2 LCDR3

<400> SEQUENCE: 15

Gln Gln Tyr Tyr Gly Tyr Pro Tyr Thr
1               5

<210> SEQ ID NO 16
<211> LENGTH: 5
<212> TYPE: PRT
<213> ORGANISM: Artificial sequence
<220> FEATURE:
<223> OTHER INFORMATION: Murine 24D5 HCDR1

<400> SEQUENCE: 16

Ser Tyr Trp Met His
1               5

<210> SEQ ID NO 17
<211> LENGTH: 17
<212> TYPE: PRT
<213> ORGANISM: Artificial sequence
<220> FEATURE:
<223> OTHER INFORMATION: Murine 24D5 HCDR2
<220> FEATURE:
<221> NAME/KEY: MISC_FEATURE
<222> LOCATION: (3)..(3)
<223> OTHER INFORMATION: Xaa is selected from H or G
<220> FEATURE:
<222> LOCATION: (8)..(8)
<223> OTHER INFORMATION: Xaa is selected from G or F

<400> SEQUENCE: 17

Arg Ile Xaa Pro Asn Ser Gly Xaa Thr Ser Tyr Asn Glu Lys Phe Lys
1               5                   10                  15

Asn

<210> SEQ ID NO 18
<211> LENGTH: 10
<212> TYPE: PRT
<213> ORGANISM: Artificial sequence
<220> FEATURE:
<223> OTHER INFORMATION: Murine 24D5 HCDR3

<400> SEQUENCE: 18

Gly Gly Ser Ser Tyr Asp Tyr Phe Asp Tyr
1               5                   10

<210> SEQ ID NO 19
<211> LENGTH: 15
<212> TYPE: PRT
<213> ORGANISM: Artificial sequence
<220> FEATURE:
<223> OTHER INFORMATION: Murine 24D5 LCDR1

<400> SEQUENCE: 19

Arg Ala Ser Glu Ser Val Ser Ile His Gly Thr His Leu Met His
1               5                   10                  15

<210> SEQ ID NO 20
<211> LENGTH: 7
<212> TYPE: PRT
<213> ORGANISM: Artificial sequence
<220> FEATURE:
<223> OTHER INFORMATION: Murine 24D5 LCDR2

<400> SEQUENCE: 20
```

```
Ala Ala Ser Asn Leu Glu Ser
1               5
```

```
<210> SEQ ID NO 21
<211> LENGTH: 9
<212> TYPE: PRT
<213> ORGANISM: Artificial sequence
<220> FEATURE:
<223> OTHER INFORMATION: Murine 24D5 LCDR3

<400> SEQUENCE: 21

Gln Gln Ser Phe Glu Asp Pro Leu Thr
1               5
```

```
<210> SEQ ID NO 22
<211> LENGTH: 118
<212> TYPE: PRT
<213> ORGANISM: Artificial sequence
<220> FEATURE:
<223> OTHER INFORMATION: Humanized heavy chain variable region sequence
      of 9-2

<400> SEQUENCE: 22

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Asp
            20                  25                  30

Tyr Trp Asn Trp Ile Arg Gln His Pro Gly Lys Gly Leu Glu Trp Ile
        35                  40                  45

Gly Tyr Ile Ser Tyr Thr Gly Ser Thr Tyr Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Gly Gly Trp Leu Ala Pro Phe Asp Tyr Trp Gly Arg Gly Thr
            100                 105                 110

Leu Val Thr Val Ser Ser
        115
```

```
<210> SEQ ID NO 23
<211> LENGTH: 113
<212> TYPE: PRT
<213> ORGANISM: Artificial sequence
<220> FEATURE:
<223> OTHER INFORMATION: Humanized light chain variable region sequence
      of 9-2

<400> SEQUENCE: 23

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Tyr Arg
            20                  25                  30

Ser Asn Gln Lys Asn Ser Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95
```

Tyr Tyr Gly Tyr Pro Tyr Thr Phe Gly Gly Thr Lys Val Glu Ile
            100                 105                 110

Lys

<210> SEQ ID NO 24
<211> LENGTH: 119
<212> TYPE: PRT
<213> ORGANISM: Artificial sequence
<220> FEATURE:
<223> OTHER INFORMATION: Humanized heavy chain variable region sequence
      of 24D5

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Arg Ile His Pro Asn Ser Gly Gly Thr Ser Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ser Tyr Asp Tyr Phe Asp Tyr Trp Gly Gln Gly
            100                 105                 110

Thr Thr Val Thr Val Ser Ser
        115

<210> SEQ ID NO 25
<211> LENGTH: 111
<212> TYPE: PRT
<213> ORGANISM: Artificial sequence
<220> FEATURE:
<223> OTHER INFORMATION: Humanized light chain variable region sequence
      of 24D5

<400> SEQUENCE: 25

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Ile His
                20                  25                  30

Gly Thr His Leu Met His Trp Tyr Gln Gln Lys Pro Gly Gln Pro Pro
            35                  40                  45

Lys Leu Leu Ile Tyr Ala Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Ser Phe
                85                  90                  95

Glu Asp Pro Leu Thr Phe Gly Gln Gly Thr Lys Leu Glu Ile Lys
            100                 105                 110

<210> SEQ ID NO 26
<211> LENGTH: 118
<212> TYPE: PRT
<213> ORGANISM: Artificial sequence
<220> FEATURE:

<223> OTHER INFORMATION: Heavy chain variable region sequence of 9-2
      after affinity maturation

<400> SEQUENCE: 26

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Asp
            20                  25                  30

Tyr Trp Thr Trp Ile Arg Gln His Pro Gly Lys Gly Leu Glu Tyr Ile
        35                  40                  45

Gly Tyr Ile Ser Tyr Thr Gly Ser Thr Tyr Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Gly Gly Trp Leu Ala Pro Phe Asp Tyr Trp Gly Arg Gly Thr
            100                 105                 110

Leu Val Thr Val Ser Ser
            115

<210> SEQ ID NO 27
<211> LENGTH: 113
<212> TYPE: PRT
<213> ORGANISM: Artificial sequence
<220> FEATURE:
<223> OTHER INFORMATION: Light chain variable sequence of 24D5 after
      affinity maturation 24D5

<400> SEQUENCE: 27

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Tyr His
            20                  25                  30

Ser Asn Gln Lys His Ser Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Gly Tyr Pro Tyr Thr Phe Gly Gly Gly Thr Lys Val Glu Ile
            100                 105                 110

Lys

<210> SEQ ID NO 28
<211> LENGTH: 119
<212> TYPE: PRT
<213> ORGANISM: Artificial sequence
<220> FEATURE:
<223> OTHER INFORMATION: Heavy chain variable region sequence of 24D5
      after affinity maturation

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

```
Trp Met His Trp Val Arg Gln Ala Pro Gly Gln Gly Leu Glu Trp Met
        35                  40                  45

Gly Arg Ile Gly Pro Asn Ser Gly Phe Thr Ser Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ser Tyr Asp Tyr Phe Asp Tyr Trp Gly Gln Gly
            100                 105                 110

Thr Thr Val Thr Val Ser Ser
        115

<210> SEQ ID NO 29
<211> LENGTH: 111
<212> TYPE: PRT
<213> ORGANISM: Artificial sequence
<220> FEATURE:
<223> OTHER INFORMATION: Light chain variable region sequence of 24D5
      after affinity maturation

<400> SEQUENCE: 29

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Glu Asp Thr Ala Asn Tyr Tyr Cys Gln Gln Ser Phe
                85                  90                  95

Glu Asp Pro Leu Thr Phe Gly Gln Gly Thr Lys Leu Glu Ile Lys
            100                 105                 110

<210> SEQ ID NO 30
<211> LENGTH: 445
<212> TYPE: PRT
<213> ORGANISM: Artificial sequence
<220> FEATURE:
<223> OTHER INFORMATION: Heavy chain region sequence of HRP00049 9-2

<400> SEQUENCE: 30

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Asn Asp
            20                  25                  30

Tyr Trp Thr Trp Ile Arg Gln His Pro Gly Lys Gly Leu Glu Tyr Ile
        35                  40                  45

Gly Tyr Ile Ser Tyr Thr Gly Ser Thr Tyr Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

```
Arg Ser Gly Gly Trp Leu Ala Pro Phe Asp Tyr Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 31
<211> LENGTH: 1338
<212> TYPE: DNA
<213> ORGANISM: Artificial sequence
<220> FEATURE:
<223> OTHER INFORMATION: DNA sequence encoding heavy chain sequence of
      HRP00049 9-2

<400> SEQUENCE: 31
caggtgcaac tgcaggagag cggccccgga ctcgtgaaac cctcccagac cctgagcctg      60
```

```
acctgtaccg tgagcggcgg cagcatcagc aacgactact ggacttggat caggcagcac    120
cccggcaaag gcctggagta catcggctac atcagctaca ccggctccac ctactacaac    180
cccagcctga agtccagggt gaccatcagc cgggacacca gcaagaacca gttcagcctg    240
aagctgagca gcgtgaccgc tgccgacaca gccgtgtact attgtgccag aagcggcgga    300
tggctggccc ctttcgacta ctggggcaga ggcaccctgg tgaccgtgag cagcgcttcc    360
accaagggcc catcggtctt ccccctggcg ccctgctcca ggagcacctc cgagagcaca    420
gccgccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcacgaa gacctacacc    600 tgcaacgtag atcacaagcc cagcaacacc aaggtggaca gagagttga gtccaaatat    660 ggtcccccat gcccaccatg cccagcacct gaggctgctg ggggaccatc agtcttcctg    720
ttccccccaa acccaagga cactctcatg atctcccgga cccctgaggt cacgtgcgtg    780
gtggtggacg tgagccagga agaccccgag gtccagttca actggtacgt ggatggcgtg    840
gaggtgcata atgccaagac aaagccgcgg gaggagcagt tcaacagcac gtaccgtgtg    900
gtcagcgtcc tcaccgtcct gcaccaggac tggctgaacg gcaaggagta caagtgcaag    960
gtctccaaca aaggcctccc gtcctccatc gagaaaacca tctccaaagc caaagggcag    1020
ccccgagagc cacaggtgta caccctgccc ccatcccagg aggagatgac caagaaccag    1080
gtcagcctga cctgcctggt caaaggcttc taccccagcg acatcgccgt ggagtgggag    1140
agcaatgggc agccggagaa caactacaag accacgcctc ccgtgctgga ctccgacggc    1200
tccttcttcc tctacagcag gctcaccgtg gacaagagca ggtggcagga ggggaatgtc    1260
ttctcatgct ccgtgatgca tgaggctctg cacaaccact acacacagaa gagcctctcc    1320
ctgtctctgg gtaaatga                                                 1338
```

<210> SEQ ID NO 32
<211> LENGTH: 220
<212> TYPE: PRT
<213> ORGANISM: Artificial sequence
<220> FEATURE:
<223> OTHER INFORMATION: Light chain sequnece of HRP00049 9-2

<400> SEQUENCE: 32

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Tyr His
            20                  25                  30

Ser Asn Gln Lys His Ser Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Gly Tyr Pro Tyr Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
```

```
            130                 135                 140
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
210                 215                 220

<210> SEQ ID NO 33
<211> LENGTH: 663
<212> TYPE: DNA
<213> ORGANISM: Artificial sequence
<220> FEATURE:
<223> OTHER INFORMATION: DNA sequence encoding light chain sequence of
      HRP00049 9-2

<400> SEQUENCE: 33
gacatcgtga tgacccagag ccctgatagc ctggctgtga gcctgggcga gagagccacc      60
atcaactgca agagcagcca gagcctgttc taccatagca accagaagca cagcctcgcc     120
tggtatcagc agaagcccgg ccaaccccca agctgctga tctacggcgc cagcacaaga      180
gagagcggag tgcccgatag gttcagcggc agcggatccg gcaccgattt cacccctgac      240
atcagcagcc tgcaggccga ggatgtggcc gtgtactact gccagcagta ctacggctac     300
ccttacacct tcggcggcgg caccaaggtg gagatcaagc gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660
tga                                                                   663

<210> SEQ ID NO 34
<211> LENGTH: 446
<212> TYPE: PRT
<213> ORGANISM: Artificial sequence
<220> FEATURE:
<223> OTHER INFORMATION: Heavy chain sequence of HRP00052 24D5

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Arg Ile Gly Pro Asn Ser Gly Phe Thr Ser Tyr Asn Glu Lys Phe
        50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

Ala Arg Gly Gly Ser Ser Tyr Asp Tyr Phe Asp Tyr Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
            210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 35
<211> LENGTH: 1341
<212> TYPE: DNA
<213> ORGANISM: Artificial sequence
<220> FEATURE:
<223> OTHER INFORMATION: DNA sequence encoding heavy chain sequence of
      HRP00052 24D5

<400> SEQUENCE: 35
caggtgcaac tggtgcagag cggtgccgag gtgaagaagc ctggcgcaag cgtgaaagtg     60

```
agctgcaagg ccagcggcta caccttcacc agctactgga tgcactgggt gaggcaggcc    120
cctggacagg gcctggagtg gatgggcagg atcgggccca acagtggttt cactagctac    180
aatgaaaagt tcaagaacag ggtaaccatg accagggaca cctccaccag cacagtgtat    240
atggagctga gcagcctgag gagcgaggac accgccgtgt actactgtgc cagaggcggc    300
agcagctacg actacttcga ctattggggc cagggcacca ccgtgaccgt gagcagtgct    360
tccaccaagg gcccatcggt cttccccctg gcgccctgct ccaggagcac ctccgagagc    420
acagccgccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac gaagacctac    600
acctgcaacg tagatcacaa gcccagcaac accaaggtgg acaagagagt tgagtccaaa    660
tatggtcccc catgcccacc atgcccagca cctgaggctg ctgggggacc atcagtcttc    720
ctgttccccc caaaacccaa ggacactctc atgatctccc ggacccctga ggtcacgtgc    780
gtggtggtgg acgtgagcca ggaagacccc gaggtccagt tcaactggta cgtggatggc    840
gtggaggtgc ataatgccaa gacaaagccg cgggaggagc agttcaacag cacgtaccgt    900
gtggtcagcg tcctcaccgt cctgcaccag gactggctga acggcaagga gtacaagtgc    960
aaggtctcca acaaaggcct cccgtcctcc atcgagaaaa ccatctccaa agccaaaggg   1020
cagccccgag agccacaggt gtacaccctg cccccatccc aggaggagat gaccaagaac   1080
caggtcagcc tgacctgcct ggtcaaaggc ttctacccca gcgacatcgc cgtggagtgg   1140
gagagcaatg ggcagccgga gaacaactac aagaccacgc tcccgtgct ggactccgac   1200 ggctccttct cctctacag caggctcacc gtggacaaga gcaggtggca ggaggggaat   1260
gtcttctcat gctccgtgat gcatgaggct ctgcacaacc actacacaca gaagagcctc   1320
tccctgtctc tgggtaaatg a                                              1341
```

<210> SEQ ID NO 36
<211> LENGTH: 218
<212> TYPE: PRT
<213> ORGANISM: Artificial sequence
<220> FEATURE:
<223> OTHER INFORMATION: Light chain of HRP00052 24D5

<400> SEQUENCE: 36

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Glu Asp Thr Ala Asn Tyr Tyr Cys Gln Gln Ser Phe
                85                  90                  95

Glu Asp Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125
```

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 37
<211> LENGTH: 657
<212> TYPE: DNA
<213> ORGANISM: Artificial sequence
<220> FEATURE:
<223> OTHER INFORMATION: DNA sequence encoding light chain sequence of
      HRP00052 24D5

<400> SEQUENCE: 37
gacatcgtgc tgacccagag tcccgcctca cttgccgtga gccccggtca gagggccacc      60
atcacctgta gggccagcga gagcgtgagc atccacggca cccacctgat gcactggtat     120
caacagaaac ccggccagcc ccccaaactg ctgatctacg ccgccagcaa cctggagagc     180
ggcgtgcccg ccaggttcag cggctccggc agcggcaccg acttcaccct cactatcaac     240
cccgtggagg ccgaggacac cgccaactac tactgccagc agagcttcga ggaccccctg     300
accttcggcc agggcaccaa gctggagatc aagcgtacgg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca agtctacgc ctgcgaagtc     600 acccatcagg gcctgagctc gcccgtcaca aagagcttca caggggaga gtgttga      657

<210> SEQ ID NO 38
<211> LENGTH: 5
<212> TYPE: PRT
<213> ORGANISM: Artificial sequence
<220> FEATURE:
<223> OTHER INFORMATION: HCDR1 of murine 9-2

<400> SEQUENCE: 38

Asn Asp Tyr Trp Asn
1               5

<210> SEQ ID NO 39
<211> LENGTH: 17
<212> TYPE: PRT
<213> ORGANISM: Artificial sequence
<220> FEATURE:
<223> OTHER INFORMATION: HCDR2 of murine 24D5

<400> SEQUENCE: 39

Arg Ile His Pro Asn Ser Gly Gly Thr Ser Tyr Asn Glu Lys Phe Lys
1               5                   10                  15

Asn

```
<210> SEQ ID NO 40
<211> LENGTH: 17
<212> TYPE: PRT
<213> ORGANISM: Artificial sequence
<220> FEATURE:
<223> OTHER INFORMATION: LCDR1 of murine 9-2

<400> SEQUENCE: 40

Lys Ser Ser Gln Ser Leu Phe Tyr Arg Ser Asn Gln Lys Asn Ser Leu
1               5                   10                  15

Ala

<210> SEQ ID NO 41
<211> LENGTH: 5
<212> TYPE: PRT
<213> ORGANISM: Artificial Sequence
<220> FEATURE:
<223> OTHER INFORMATION: Linker

<400> SEQUENCE: 41

Gly Gly Gly Gly Ser
1               5
```

PD-L1 ANTIBODY, ANTIGEN-BINDING FRAGMENT THEREOF AND MEDICAL APPLICATION THEREOF

CROSS-REFERENCE TO RELATED APPLICATION

This application is a divisional of U.S. application Ser. No. 15/775,598, filed May 11, 2018, which is a Section 371 of International Application No. PCT/CN2016/104320, filed Nov. 2, 2016, which was published in the Chinese language on May 26, 2017, under International Publication No. WO 2017/084495 A1, which claims priority under 35 U.S.C. § 119(b) to Chinese Application No. 201510788907.3, filed Nov. 17, 2015, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "065825_58US2_Sequence_Listing" and a creation date of Aug. 7, 2020, and having a size of about 49 kb. The sequence listing submitted via EFS-Web is part of the specification and is herein incorporated by reference in its entirety.

FIELD OF THE INVENTION

The present invention relates to a PD-L1 antibody, antigen-binding fragment thereof, a chimeric antibody, and a humanized antibody comprising the CDR regions of a PD-L1 antibody, as well as a pharmaceutical composition comprising a PD-L1 antibody or an antigen-binding fragment thereof, and its use as an anti-cancer drug.

BACKGROUND OF THE INVENTION

Tumor immunotherapy has been a hot area in tumor therapeutics for a long time, wherein T cell-associated immunotherapy is one of the main pillars. Tumor immunotherapy kills tumors by fully utilizing and mobilizing cytotoxic T lymphocytes in patients. It may be the most effective and safest way for cancer treatment. At the same time, tumor escape is a huge obstacle faced by tumor immunotherapy, in which the rapid proliferation of the cancer cells is promoted via their inhibitory effect on the immune system.

There is an extremely complicated relationship between the mechanism underlying the tumor immune escape and the body's immune response to tumors. In the early stages of tumor immunotherapy, tumor-specific killer T cells have biological activity, but lose the killing function as the tumor progresses into late stages. Thus, tumor immunotherapy is aimed to maximize the patient's own immune system response to the tumor. It is essential in tumor immunotherapy to not only activate the innate immune system response, but also maintain the duration and intensity of the immune response.

A human T-cell is activated in vivo via a two-signaling-pathway system, wherein antigen-presenting cells are needed to present MHC-antigen peptide to T cells to provide a first signal. Then a series of co-stimulatory molecules are required to provide a second signal to enable T cells to exhibit a normal immune response. This double-signaling system plays a vital role in balancing the in vivo immune system and strictly regulates different immune responses to endogenous and exogenous antigens, respectively. The absence of a second signal provided by co-stimulatory molecules will result in no response or sustained-specific T cell immune response and consequently lead to tolerance. Therefore, the second signaling pathway plays a key regulatory role in the whole process of the immune response.

Programmed death-1 (PD-1), found in 1992, is a protein receptor expressed on the surface of T cells and is involved in cell apoptosis. PD-1 belongs to the CD28 family and exhibits 23% homology in amino acid sequence with cytotoxic T lymphocyte antigen 4 (CTLA-4). Unlike CTLA4, PD-1 is mainly expressed on the activated T cells, B cells and myeloid cells. PD-1 has two ligands, PD-L1 and PD-L2. PD-L1 is mainly expressed on the T cells, B cells, macrophages, and dendritic cells (DC), and the expression will be up-regulated after activation of the cells. The expression of PD-L2 is relatively limited to antigen-presenting cells, such as activated macrophages and dendritic cells.

PD-L1 binds to PD-1 and B7-1 to inhibit the immune system, and many tumor cells and immune cells in tumor microenvironment express PD-L1. New studies have detected high expression of PD-L1 protein in human tumor tissues such as breast cancer, lung cancer, gastric cancer, intestinal cancer, renal cancer, melanoma, non-small cell lung cancer, colon cancer, bladder cancer, ovarian cancer, pancreatic cancer, liver cancer and others. Additionally, the expression level of PD-L1 is closely correlated with clinical condition and prognosis of patients.

As PD-L1 inhibits T cell proliferation through the second signaling pathway, blocking the binding of PD-L1 and PD-1 becomes a very promising target in the tumor immunotherapy field.

Currently there are several multinational pharmaceutical companies engaging in the study of monoclonal antibodies against PD-L1. These antibodies maximize the self-immune response of patients against tumors by blocking the binding of PD-1 and PD-L1 and sequentially kill tumor cells. Related patents are, for example, WO0139722, WO2013173223, WO2014195852, WO2013181634, WO2015048520, WO2015036511, US2014335093, WO2014100079, WO2014055897, U.S. Pat. No. 6,803,192B1, WO2014022758, U.S. Pat. No. 8,617,546B2 and WO2010089411A2.

The present invention provides a PD-L1 antibody with high affinity, high selectivity, and high biological activity.

SUMMARY OF THE INVENTION

The present invention provides a PD-L1 antibody or an antigen-binding fragment thereof, comprising any one of the CDR region sequences selected from the following or a mutant sequence thereof:
  heavy chain variable region HCDR sequences shown in: SEQ ID NOs: 10-12 or SEQ ID NOs: 16-18; and light chain variable region LCDR sequence shown in: SEQ ID NOs: 13-15 or SEQ ID NOs: 19-21;
  Specifically, as follows:
  HCDR1 selected from NDYWX$_1$ (SEQ ID NO: 10) or SYWMH (SEQ ID NO: 16);
  HCDR2 selected from YISYTGSTYYNPSLKS (SEQ ID NO: 11) or RI X$_4$PNSG X$_5$TSYNEKFKN (SEQ ID NO: 17):
  HCDR3 selected from SGGWLAPFDY (SEQ ID NO: 12) or GGSSYDYFDY (SEQ ID NO: 18);

LCDR1 selected from KSSQSLFYX₂SNQKX₃SLA (SEQ ID NO: 13) or RASESVSIHGTHLMH (SEQ ID NO: 19);

LCDR2 selected from GASTRES (SEQ ID NO: 14) or AASNLES (SEQ ID NO: 20);

LCDR3 selected from QQYYGYPYT (SEQ ID NO: 15) or QQSFEDPLT (SEQ ID NO: 21);

Wherein $X_1$ is selected from N or T, $X_2$ is selected from R or H, $X_3$ is selected from N or H, $X_4$ is selected from H or G, and $X_5$ is selected from G or F.

In a preferred embodiment of the present invention, a PD-L1 antibody or antigen-binding fragment thereof, according to the present invention comprises a heavy chain variable region HCDR sequence selected from the group consisting of SEQ ID NO: 10, SEQ ID NO: 11, SEQ ID NO: 12, SEQ ID NO: 16, SEQ ID NO: 17 and SEQ ID NO: 18, or a mutant sequence thereof.

In another preferred embodiment of the present invention, a PD-L1 antibody or antigen-binding fragment thereof, according to the present invention comprises a light chain variable region LCDR sequence selected from the group consisting of SEQ ID NO: 13, SEQ ID NO: 14, SEQ ID NO: 15, SEQ ID NO: 19, SEQ ID NO: 20 and SEQ ID NO: 21, or a mutated sequence thereof.

In another preferred embodiment of the present invention, a PD-L1 antibody or antigen-binding fragment thereof according to the present invention, wherein the antibody light chain variable region further comprises a light chain FR region derived from murine κ chain, or a variant thereof, or a light chain FR region derived from murine λ-chain, or a variant thereof, wherein the antibody heavy chain variable region further comprises a heavy chain FR region derived from murine IgG1, or a variant thereof, or a heavy chain FR region derived from murine IgG2, or a variant thereof, or a heavy chain FR region derived from murine IgG3, or a variant thereof.

In another preferred embodiment of the present invention, a PD-L1 antibody or antigen-binding fragment thereof according to the present invention, wherein the antibody heavy chain variable region containing a murine-derived FR region is selected from the group consisting of SEQ ID NOs: 6 and 8, or a mutant sequence thereof, wherein the antibody light chain variable region containing a murine-derived FR region is selected from the group consisting of SEQ ID NOs: 7 and 9, or a mutant sequence thereof.

In another preferred embodiment of the present invention, a PD-L1 antibody or antigen-binding fragment thereof according to the present invention, wherein the antibody light chain further comprises a light chain constant region derived from murine κ chain, or a variant thereof, or a light chain constant region derived from murine λ chain, or a variant thereof, wherein the antibody heavy chain further comprises a heavy chain constant region derived from murine IgG1, or a variant thereof, or a heavy chain constant region derived from murine IgG2 or a variant thereof, or a heavy chain constant region derived from murine IgG3, or a variant thereof.

In another preferred embodiment of the present invention, a PD-L1 antibody or antigen-binding fragment thereof according to the present invention is a chimeric antibody. A PD-L1 chimeric antibody or the fragment thereof provided herein further comprises a heavy chain constant region derived from human IgG1, IgG2, IgG3, or IgG4, or a variant thereof, preferably comprises a heavy chain constant region derived from human IgG2, or IgG4, or IgG1 without ADCC (antibody-dependent cell-mediated cytotoxicity) via amino acid mutation.

In another preferred embodiment of the present invention, a PD-L1 antibody or antigen-binding fragment thereof according to the present invention is a humanized antibody or the fragment thereof. Preferably, the humanized antibody provided herein is the humanized antibody 9-2 or the humanized antibody 24D5, and the heavy chain FR sequence on the heavy chain variable region of the humanized antibody provided herein is derived from a human germline heavy chain, wherein: the heavy chain FR sequence on the heavy chain variable region of the humanized antibody 9-2 is derived from a combination sequence of a human germline heavy chain IGHV4-30-4*01 and hjh2, and comprises FR1, FR2, FR3 from human germline heavy chain IGHV4-30-4*01 and FR4 from hjh2; the heavy chain FR sequence on the heavy chain variable region of the humanized antibody 24D5 is derived from a combination sequence of a human germline heavy chain IGHV1-46*01 and hjh6.1, and comprises FR1, FR2, FR3 from human germline heavy chain IGHV1-46*01 and FR4 from hjh6.1. More preferably, the heavy chain FR sequence of the humanized antibody 9-2 provided herein has 0-10 amino acid back-mutations, preferably has one or more amino acid back-mutations selected from the group consisting of W47Y, V71R, G27Y, I48M, V67L, F78Y, S30T, and Q39K, more preferably has W47Y and V71R amino acid back-mutations; the heavy chain FR sequence of the humanized antibody 24D5 provided herein has 0-10 amino acid back-mutations, preferably has one or more amino acid back-mutations selected from the group consisting of T74K, R72V, M48I, M70L, R38Q, L83F, V68A, and V79A. Further, more preferably, the heavy chain variable region sequence of the humanized antibody is as follows: the heavy chain variable region sequence of the humanized antibody 9-2 is shown in SEQ ID NO: 22, or a variant thereof; or the heavy chain variable region sequence of the humanized antibody 24D5 is shown in SEQ ID NO: 24, or a variant thereof.

In another preferred embodiment of the present invention, a PD-L1 antibody or antigen-binding fragment thereof according to the present invention is a humanized antibody or the fragment thereof. Preferably, the humanized antibody provided herein is the humanized antibody 9-2 or the humanized antibody 24D5, the light chain FR sequence on the light chain variable region of the humanized antibody provided herein is derived from a human germline light chain, wherein: the light chain FR sequence on the light chain variable region of the humanized antibody 9-2 is derived from a combination sequence of a human germline light chain IGKV4-1*01 and hjk4.1, and comprises FR1, FR2 and FR3 from human germline light IGKV4-1*01 and FR4 from hjk4.1: the light chain FR sequence on the light chain variable region of the humanized antibody 24D5 is derived from a combination sequence of a human germline light chain IGKV7-3*01 and hjk2.1, and comprises FR1, FR2 and FR3 from human germline light IGKV7-3*01 and FR4 from hjk2.1. Preferably, the light chain FR sequence of the humanized antibody 9-2 provided herein has 0-10 amino acid back-mutations, more preferably has a P49S amino acid back-mutation. The light chain FR sequence of the humanized antibody 24D5 provided herein has 0-10 amino acid back-mutations, preferably has one or more amino acid back-mutations selected from the group consisting of Y91F, T22S and G72E, or introducing N85E deglycosylation mutation. Further, more preferably, the light chain variable region sequence of the humanized antibody provided herein is shown as follows: the light chain variable region sequence of the humanized antibody Ab-1 is shown in SEQ ID NO: 23, or a variant thereof; or the light chain variable region sequence of the humanized antibody Ab-2 is shown in SEQ ID NO: 25, or a variant thereof.

In another preferred embodiment of the present invention, provided is a PD-L1 antibody or antigen-binding fragment thereof, wherein the humanized antibody or antigen-binding fragment thereof is subjected to an affinity maturation design.

In another preferred embodiment of the present invention, provided is a PD-L1 antibody or antigen-binding fragment thereof, wherein $X_1$ is T, $X_2$ is H, $X_3$ is H, $X_4$ is G, $X_5$ is F.

In another preferred embodiment of the present invention, a PD-L1 antibody or antigen-binding fragment thereof comprises the humanized antibody variable region sequence as follows:
the heavy chain variable region sequence of the humanized antibody 9-2 comprises SEQ ID NO: 26; and the light chain variable region sequence of the humanized antibody 9-2 comprises SEQ ID NO: 27;
the heavy chain variable region sequence of the humanized antibody 24D5 comprises SEQ ID NO: 28; and the light chain variable region sequence of the humanized antibody 24D5 comprises SEQ ID NO: 29.

In another preferred embodiment of the present invention, a PD-L1 antibody or antigen-binding fragment provided herein is humanized antibody or fragment thereof, wherein the heavy chain of humanized antibody further comprises a heavy chain constant region derived from human IgG1, IgG2, IgG3, or IgG4, or a variant thereof, preferably comprises a heavy chain constant region derived from human IgG2 or IgG4, more preferably comprises IgG4 heavy chain Fc region with F234A and L235A mutations; the humanized antibody further comprises a light chain constant region derived from human κ chain, human λ chain, or a variant thereof.

In another preferred embodiment of the present invention, a PD-L1 antibody or antigen-binding fragment thereof provided herein is the humanized antibody 9-2 or the humanized antibody 24D5, wherein the humanized antibody 9-2 comprises the heavy chain antibody sequence of SEQ ID NO: 30, and the light chain antibody sequence of SEQ ID NO: 32; wherein the humanized antibody 24D5 comprises the heavy chain antibody sequence of SEQ ID NO: 34, and the light chain antibody sequence of SEQ ID NO: 36.

The present invention further provides a pharmaceutical composition which comprises a therapeutically effective amount of the PD-L1 antibody or the antigen-binding fragment thereof described herein and one or more pharmaceutically acceptable carrier, diluent or excipient.

The present invention further provides a DNA molecule encoding the PD-L1 antibody or the antigen-binding fragment thereof described above.

The present invention further provides an expression vector comprising the DNA molecule encoding the PD-L1 antibody or the antigen-binding fragment thereof as described above.

The present invention further provides a host cell transformed with the expression vector as described above, wherein the host cell is selected from the group consisting of bacteria, yeast, and mammalian cells: preferably mammalian cells.

In another preferred embodiment of present invention, the host cell described herein is bacterium, preferably *E. coli*.

In another preferred embodiment of present invention, the host cell described herein is yeast, preferably *Pichia pastoris*.

In another preferred embodiment of present invention, a PD-L1 antibody or the antigen-binding fragment thereof is provided herein, wherein the antigen-binding fragment is Fab, Fv, scFv or F(ab')2.

The present invention further provides use of the above PD-L1 antibody or the antigen-binding fragment thereof, or the pharmaceutical composition containing the same, in the preparation of a medicament for treatment of a PD-L1 mediated disease or disorder, wherein the disease is preferably a cancer, more preferably is a PD-L1-expressing cancer; and the cancer is preferably selected from the group consisting of breast cancer, lung cancer, stomach cancer, intestinal cancer, renal cancer, melanoma and bladder cancer; and most preferably is selected from the group consisting of non-small cell lung cancer, melanoma, bladder cancer and renal cancer.

The present invention further provides a method for treating or preventing a PD-1 mediated disease or disorder, comprising administering to a subject in need thereof a therapeutically effective amount of a PD-L1 antibody or the antigen-binding fragment thereof according to the invention, or the pharmaceutical composition comprising the same; wherein the disease is preferably a cancer, more preferably a PD-L1-expressing cancer: the cancer is preferably selected from the group consisting of breast cancer, lung cancer, stomach cancer, intestinal cancer, renal cancer, melanoma and bladder cancer; and most preferably is selected from the group consisting of non-small cell lung cancer, melanoma, bladder cancer and renal cancer.

DETAILED DESCRIPTION OF THE INVENTION

Terms

Figure 1:
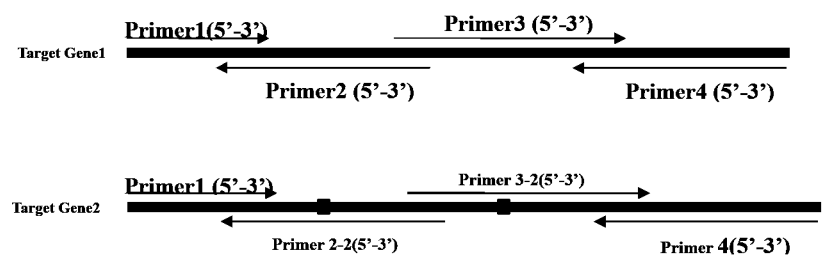
FIG. 1: Schematic diagram of primers designed for constructing a humanized clone

In order to make the invention more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, the single-letter code and the three-letter code for amino acids are as described in J. Biol. Chem, 243, (1%8) p3558.

As used herein, "Antibody" refers to immunoglobulin, a tetra-peptide chain structure connected together by disulfide bonds between two identical heavy chains and two identical light chains. Different immunoglobulin heavy chain constant regions exhibit different amino acid compositions and rank orders, hence present different kinds of antigenicity. Accordingly, immunoglobulins can be divided into five categories, or referred to as immunoglobulin isotypes, namely IgM, IgD, IgG, IgA and IgE, the corresponding heavy chains are μ chain, δ chain, γ chain, α chain and ε chain, respectively. According to its hinge region amino acid composition and the number and location of heavy chain disulfide bonds, the same isotype of Ig can be divided into different sub-categories; for example, IgG can be divided into IgG1, IgG2, IgG3, and IgG4. Light chain can be divided into κ or λ chain considering different constant regions. Each of the five Ig isotypes can have κ or λ chain.

In the present invention, the antibody light chain variable region mentioned herein further comprises a light chain constant region, which comprises a human- or murine-derived κ chain, λ chain, or a variant thereof.

In the present invention, the antibody heavy chain variable region mentioned herein further comprises a heavy chain constant region, which comprises a human- or murine-derived IgG1, IgG2, IgG3, IgG4, or a variant thereof.

About 110 amino acid sequences adjacent to the N-terminus of the antibody heavy and light chains are highly variable, known as the variable region (Fv region): the rest of the amino acid sequences near the C-terminus are relatively stable, known as the constant region. Variable region comprises three hypervariable regions (HVR) and four relatively conserved framework regions (FR). The three hypervariable regions determine the specificity of the antibody, also known as complementarity determining region (CDR). Each light chain variable region (LCVR) and each heavy chain variable region (HCVR) is composed of three CDR regions and four FR regions, with sequential order from the amino terminus to the carboxyl terminus being: FR1, CDR1, FR2, CDR2, FR3, CDR3, and FR4. The three light chain CDRs refer to LCDR1, LCDR2, and LCDR3; and the three heavy chain CDRs refer to HCDR1, HCDR2 and HCDR3. The number and location of CDR region amino acid residues in LCVR and HCVR regions of the antibody or antigen binding fragment herein comply with the known Kabat numbering criteria (LCDR1-3, HCDE2-3), or comply with Kabat and Chothia numbering criteria (HCDR1).

The antibody of the present invention comprises a murine-derived antibody, a chimeric antibody and a humanized antibody, preferably a humanized antibody.

The term "murine-derived antibody" in the present invention refers to a monoclonal antibody against human PD-L1 prepared according to the knowledge and skills in the field. During the preparation, a test subject was injected with PD-L1 antigen and then a hybridoma expressing the antibody with desired sequences or functional characteristics was isolated. In a preferred embodiment of the present invention, the murine-derived PD-L1 antibody or antigen binding fragment thereof further comprises a light chain constant region derived from murine κ chain, λ chain, or a variant thereof, or further comprises a heavy chain constant region derived from murine IgG1, IgG2, IgG3 or IgG4, or a variant thereof.

The term "chimeric antibody", is an antibody formed by fusing the variable region of a murine-derived antibody with the constant region of a human antibody, wherein the chimeric antibody can alleviate the immune response induced by the murine-derived antibody. In order to establish a chimeric antibody, a hybridoma secreting a specific murine-derived monoclonal antibody is first established. A variable region gene is cloned from mouse hybridoma cells and then a constant region gene of a human antibody is cloned as desired. The mouse variable region gene is ligated with human constant region gene to form a chimeric gene, which will then be inserted into a human vector, and finally the chimeric antibody molecule is expressed in a eukaryotic or prokaryotic industrial system. In a preferred embodiment of the present invention, the light chain variable region of PD-L1 chimeric antibody further comprises a light chain Fc region derived from human κ chain, λ chain, or a variant thereof. The heavy chain variable region of the PD-L1 chimeric antibody further comprises a heavy chain constant region derived from human IgG1, IgG2, IgG3, IgG4, or a variant thereof. The constant region of a human antibody is selected from the heavy chain constant region derived from human IgG1, IgG2, IgG3 or IgG4, or a variant thereof, and preferably comprises a heavy chain constant region derived from human IgG2 or IgG4, or IgG4 without ADCC (antibody-dependent cell-mediated cytotoxicity) via amino acid mutation.

The term "humanized antibody", also known as CDR-grafted antibody, refers to an antibody generated by grafting murine CDR sequences into a variable region framework of a human antibody, namely, the sequence of a human germline antibody framework of a different type. Humanized antibody overcomes the disadvantageously strong antibody response induced by the chimeric antibody that carries a large amount of murine protein components. Such framework sequences can be obtained from public DNA databases covering germline antibody gene sequences or published references. For example, germline DNA sequences of human heavy and light chain variable region genes can be found in "VBase" human germline sequence database (available on web www.mrccpe.com.ac.uk/vbase), as well as in Kabat, E A, et al, 1991 Sequences of Proteins of Immunological Interest, 5th Ed. To avoid the decrease in activity caused by reducing the immunogenicity, the variable region frame sequence of the human antibody is subjected to a minimum back-mutation or repeated mutation to maintain the activity. The humanized antibody of the present invention also comprises a humanized antibody wherein the CDR affinity is further matured via phage display.

As used herein, "antigen-binding fragment" refers to Fab fragment, Fab' fragment, F(ab')2 fragment with antigen-binding activity, as well as Fv fragment scFv fragment binding with human PD-L1; it comprises one or more CDR regions of antibodies described in the present invention, selected from the group consisting of SEQ ID NOs:10-21. Fv fragment is a minimum antibody fragment comprising a heavy chain variable region, a light chain variable region, and all antigen-binding sites without a constant region. Generally, Fv antibody further comprises a polypeptide linker between the VH and VL domains and is capable of forming a structure required for antigen binding. Also, different linkers can be used to connect the variable regions of two antibodies to form a polypeptide, named single chain antibody or single chain Fv (scFv). As used herein, the term "binding with PD-L1" means capable of interacting with human PD-L1. As used herein, the term "antigen-binding sites of the present invention" refers to discontinuous, three-dimensional sites on the antigen, recognized by the antibody or the antigen-binding fragment of the present invention.

As used herein, the term "ADCC", namely antibody-dependent cell-mediated cytotoxicity, refers to the cells expressing Fc receptors that directly kill the target cells coated by an antibody by recognizing the Fc segment of the antibody. ADCC effector function of the antibody can be reduced or eliminated by modifying the Fc segment in IgG. The modification refers to mutations on the antibody heavy chain constant region, such as mutations selected from N297A, L234A, L235A in IgG1: IgG2/4 chimera; or L234A/E235A mutations in IgG4.

As used herein, a fusion protein described in the present invention is a protein product obtained by co-expressing two genes via recombinant DNA technology. Recombinant PD-L1 extracellular domain Fc fusion protein is obtained by co-expressing a PD-L1 extracellular domain and a human antibody Fc fragment via recombinant DNA technology. The PD-L1 extracellular domain refers to the moiety of the PD-L1 outside cytomembrane, the sequence of which is the underlined region of SEQ ID NO: 4 below.

Methods for producing and purifying antibodies and antigen-binding fragments are well known in the art and can be found, for example, in Antibody Experimental Technology Guide of Cold Spring Harbor, Chapters 5-8 and 15. For example, mice can be immunized with human PD-L1, or fragments thereof, and the resulting antibodies can then be renatured, purified and sequenced using conventional methods well known in the art. Antigen-binding fragments can also be prepared by conventional methods. The antibody or the antigen-binding fragment of the present invention is genetically engineered to introduce one or more human framework regions (FRs) to a non-human derived CDR Human FR germline sequences can be obtained by aligning human antibody variable region from gene database and MOE software, from ImMunoGeneTics (IMGT) via their website http://imgt.cines.fr, or from The Immunoglobulin FactsBook, 20011SBN012441351.

The engineered antibody or antigen-binding fragment of the present invention can be prepared and purified using conventional methods. For example, cDNA sequences encoding a heavy chain (SEQ ID NO: 30) and a light chain (SEQ ID NO: 32) can be cloned and recombined into a GS expression vector. The recombined immunoglobulin expression vector can then stably transfect CHO cells. As a more recommended method well known in the art, mammalian expression system will make antibodies glycosylated, typically at the highly conserved N-terminus in the Fc region. Stable clones can be obtained through expression of an antibody specifically binding to human PD-L1. Positive clones can be expanded in a serum-free culture medium for antibody production in bioreactors. Culture medium, into which an antibody has been secreted, can be purified by conventional techniques. For example, the medium can be conveniently applied to a Protein A or G Sepharose™ FF column that has been equilibrated with a compatible buffer. The column is washed to remove nonspecific binding components. The bound antibody is eluted by pH gradient and the antibody fragments are detected by SDS-PAGE, and then pooled. The antibody can be filtered and concentrated using common techniques. Soluble aggregate and multimers can be effectively removed by common techniques, including size exclusion or ion exchange. The obtained product can be immediately frozen, for example at −70° C., or can be lyophilized.

"Administration" and "treatment," as they apply to an animal, human, experimental subject, cell, tissue, organ, or biological fluid, refer to contacting an exogenous pharmaceutical, therapeutic, diagnostic agent, or composition with the animal, human, subject, cell, tissue, organ, or biological fluid. "Administration" and "treatment" can refer, e.g., to therapeutic, pharmacokinetic, diagnostic, research, and experimental methods. Treatment of a cell encompasses contacting a reagent with the cell, as well as contacting a reagent with a fluid, where the fluid is in contact with the cell. "Administration" and "treatment" also mean in vitro and ex vivo treatments, e.g., of a cell, by a reagent, diagnostic, binding compound, or by another cell. "Treatment," as it applies to a human, veterinary, or a research subject, refers to therapeutic treatment, prophylactic or preventative measures, to research and diagnostic applications.

"Treat" means to administer a therapeutic agent, such as a composition comprising any of the binding compounds of the present invention, internally or externally to a patient having one or more disease symptoms for which the agent has known therapeutic activity. Typically, the agent is administered in an amount effective to alleviate one or more disease symptoms in the treated patient or population, whether by inducing the regression of or inhibiting the progression of such symptom(s) to any clinically measurable degree. The amount of a therapeutic agent that is effective to alleviate any particular disease symptom (also referred to "therapeutically effective amount") can vary according to factors such as the disease state, age, and weight of the patient, and the ability of the drug to elicit a desired response in the patient. Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the disease symptom(s) of interest in every patient, it should alleviate the target disease symptom(s) of interest in a statistically significant number of patients as determined by any statistical test known in the art such as the Student's t-test, the chi-square test, the U-test according to Mann and Whitney, the Kruskal-Wallis test (H-test). Jonckheere-Terpstra-test and the Wilcoxon-test.

"Conservative modification" or "conservative replacement or substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitution in non-essential regions of a polypeptide does not substantially alter biological activity (see, e.g., Watson et al. (1987) Molecular Biology of the Gene, The Benjamin/Cummings Pub Co., p. 224 (4.sup.th Ed.)). In addition, substitutions of structurally or functionally similar amino acids are less likely to disrupt biological activity.

"Effective amount" encompasses an amount sufficient to ameliorate or prevent a symptom or sign of a medical condition. Effective amount also means an amount sufficient to allow or facilitate diagnosis. An effective amount for a particular patient or veterinary subject can vary depending on factors such as the condition being treated, the general health of the patient, the route and dose of administration and the severity of side effects. An effective amount can be the maximal dose or dosing regimen that avoids significant side effects or toxic effects.

"Exogenous" refers to substances that are produced outside an organism, cell, or human body, depending on the context. "Endogenous" refers to substances that are produced within a cell, organism, or human body, depending on the context.

"Homology" refers to sequence similarity between two polynucleotide sequences or between two polypeptides. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared and then multiplied by 100. For example, if 6 of 10 positions in two sequences are matched or homologous when the sequences are optimally aligned, then the two sequences are 60% homologous. Generally, the comparison is made when two sequences are aligned to give maximum percent homology.

As used herein, the expressions "cell," "cell line," and "cell culture" are used interchangeably and all such designations include progeny. Thus, the words "transformants" and "transformed cells" include the primary subject cell and cultures derived therefrom without considering the number of passages. It is also understood that all progeny may not be precisely identical in DNA content, due to deliberate or inadvertent mutations. Mutated progeny that have the same function or biological activity as screened for in the originally transformed cell are included. Where distinct designations are intended, it will be clear from the context.

As used herein, "polymerase chain reaction" or "PCR" refers to a procedure or technique in which minute amounts of a specific moiety of nucleic acid, RNA and/or DNA, are amplified as described in, e.g., U.S. Pat. No. 4,683,195. Generally, sequence information from or beyond the ends of the region of interest needs to be available, such that oligonucleotide primers can be designed; these primers will be identical or similar in sequence to the corresponding strands of the template to be amplified. The 5' terminal nucleotides of the two primers can be identical with the ends of the material to be amplified. PCR can be used to amplify specific RNA sequences, specific DNA sequences from total genomic DNA, and cDNA transcribed from total cellular RNA, bacteriophage, or plasmid sequences, etc. See generally Mullis et al. (1987) Cold Spring Harbor Symp. Ouant. Biol. 51:263; Erlich, ed., (1989) PCR TECHNOLOGY (Stockton Press, N.Y.). As used herein, PCR is considered as one, but not the only, example of a nucleic acid polymerase reaction method for amplifying a nucleic acid test sample, comprising the use of a known nucleic acid as a primer and a nucleic acid polymerase to amplify or generate a specific moiety of the nucleic acid.

"Optional" or "optionally" means that the event or situation that follows can but does not necessarily occur, and the description includes the instances in which the event or circumstance does or does not occur. For example, "optionally comprises 1-3 antibody heavy chain variable regions" means the antibody heavy chain variable region with specific sequence can be, but not necessarily be present.

"Pharmaceutical composition" refers to a mixture comprising one or more compounds according to the present invention or a physiologically/pharmaceutically acceptable salt or prodrug thereof with other chemical components, as well as additional components such as physiologically/pharmaceutically acceptable carriers and excipients. The pharmaceutical composition aims at promoting the administration to an organism, facilitating the absorption of the active ingredient and thereby exerting a biological effect.

EXAMPLES AND TESTS

Hereinafter, the present invention is further described with reference to the examples. However, the scope of the present invention is not limited thereto. In the examples of the present invention, where specific conditions are not described, the experiments are generally conducted under conventional conditions as described in Antibody Technology Laboratory Manual and Molecular Cloning Manual of Cold Spring Harbor, or under conditions proposed by the material or product manufacturers. Where the source of the reagents is not specifically given, the reagents are commercially available conventional reagents.

Example 1. Preparation of the PD-L1 Antigen and the Detection Protein Design and Expression of the Protein The full-length human PD-L1 gene (UniProt Programmed Cell Death1 Ligand1 (PD-L1) isoform1 (SEQ ID NO: 1), from Sino Biological Inc., (HG10084-M)) was used as the template for PD-L1 of the present invention to obtain the gene sequences encoding antigens and the detection proteins of the present invention. Optionally, recombined with the antibody heavy chain Fc fragment (e.g., human IgG1), cloned into pTT5 vector (Biovector, Cat #: 102762) or pTargeT™ vector (promega, A1410) respectively, transiently expressed in 293F cells (Invitrogen, R79007) or stable expressed in CHO-S cells (Invitrogen, k9000-20), and purified to obtain the antigen and detection proteins of the present invention. Human PD-1 gene was purchased from ORIGENE, No. SC117011, NCBI Reference Sequence: NM_005018.1.

1. Human PD-L1 Full Length Amino Acid Sequence

SEQ ID NO: 1
MRIFAVFIFM TYWHLLNAFT VTVPKDLYVV EYGSNMTIEC

KFPVEKQLDL AALIVYWEME DKNIIQFVHG EEDLKVQHSS

YRQRARLLKD QLSLGNAALQ ITDVKLQDAG VYRCMISYGG

ADYKRITVKV NAPYNKINQR ILVVDPVTSE HELTCQAEGY

PKAEVIWTSS DHQVLSGKTT TTNSKREEKL FNVTSTLRIN

TTTNEIFYCT FRRLDPEENH TAELVIPELP LAHPPNERTH

LVILGAILLC LGVALTFIFR *LRKGRMMDVK KCGIQDTNSK*

*KQSDTHLEET*

Double underlined portion represents a signal peptide (Signal peptide: from 1 to 18).

Underlined portion represents extracellular domain of PD-L1 (Extracellular domain: from 19 to 238), wherein, from 19 to 127 represents Ig-like V-type Domain, and from 133 to 225 represents Ig-like C2-type Domain.

Dotted line portion represents transmembrane region (Transmembrane domain: from 239 to 259).

Italic portion represents cytoplasmic domain (Cytoplasmic domain: from 260 to 290).

2. Immunogen: PD-L1 with his, PADRE Tag: PD-L1 (Extra Cellular Domain, Short of ECD)-PADRE-His6

SEQ ID NO: 2
FT VTVPKDLYVV EYGSNMTIEC KFPVEKQLDL AALIVYWEME

DKNIIQFVHG EEDLKVQHSS YRQRARLLKD QLSLGNAALQ

ITDVKLQDAG VYRCMISYGG ADYKRITVKV NAPYNKINQR

ILVVDPVTSE HELTCQAEGY PKAEVIWTSS DHQVLSGKTT

TTNSKREEKL FNVTSTLRIN TTTNEIFYCT FRRLDPEENH

TAELVIPELP LAHPPNERGS GAKFVAAWTL KAAA*HHHHHH*

Underlined portion represents extracellular domain of PD-L1; Dotted line portion represents PADRE tag: Italic portion represents His6-tag.

3. PD-L1 with FLAG and HIS Tag (PD-L1 (ECD)-Flag-His6) was Obtained and was Used for the Performance Test of the Antibodies of the Present Invention.

SEQ ID NO: 3

FT VTVPKDLYVV EYGSNMTIEC KFPVEKQLDL AALIVYWEME

DKNIIQFVHG EEDLKVQHSS YRQRARLLKD QLSLGNAALQ

ITDVKLQDAG VYRCMISYGG ADYKRITVKV NAPYNKINQR

ILVVDPVTSE HELTCQAEGY PKAEVIWTSS DHQVLSGKTT

TTNSKREEKL FNVTSTLRIN TTTNEIFYCT FRRLDPEENH

TAELVIPELP LAHPPNERDY KDDDDK*HHHH HH*

Underlined portion presents extracellular domain of PD-L1: Dotted line portion represents Flag-Tag-, Italic portion represents His6-tag.

4. PD-L1 Fc Fusion Protein: PD-L1 (ECD)-Fc, is Used as an Immuno Antigen or a Detection Reagent of the Present Invention.

VKL-PD-L1(ECD)-Fc(human IgG1)

SEQ ID NO: 4

FTVTVPKDLYVVEYGSNMTIECKFPVEKQLDLAALIVYWEMEDKNIIQFV

HGEEDLKVQHSSYRQRARLLKDQLSLGNAALQITDVKLQDAGVYRCMISY

GGADYKRITVKVNAPYNKINQRILVVDPVTSEHELTCQAEGYPKAEVIWT

SSDHQVLSGKTTTTNSKREEKLFNVTSTLRINTTTNEIFYCTFRRLDPEE

NHTAELVIPELPLAHPPNER*DKTHTCPPCPAPELLGGPSVFLFPPKPKDT*

*LMISRTPEVTCVVVDVSHEDPEVKFNWYVDGVEVHNAKTKPREEQYNSTY*

*RVVSVLTVLHQDWLNGKEYKCKVSNKALPAPIEKTISKAKGQPREPQVYT*

*LPPSREEMTKNQVSLTCLVKGFYPSDIAVEWESNGQPENNYKTTPPVLDS*

*DGSFFLYSKLTVDKSRWQQGNVFSCSVMHEALHNHYTQKSLSLSPGK*

Underlined portion represents extracellular domain of PD-L1; Italic portion represents human IgG Fc.

5. PD-1 Fc Fusion Protein: PD-1(ECD)-Fc, is Used for the Performance Test of Antibodies of the Present Invention.

SEQ ID NO: 5

PGWFLDSPDRPWNPPTFSPALLVVTEGDNATFTCSFSNTSESFVLNWYRM

SPSNQTDKLAAFPEDRSQPGQDCRFRVTQLPNGRDFHMSVVRARRNDSGT

YLCGAISLAPKAQIKESLRAELRVTERRAEVETAHPSPSPRPAGQFQTLV

*EPKSSDKTHTCPPCPAPELLGGPSVFLFPPKPKDTLMISRTPEVTCVVVD*

*VSHEDPEVKFNWYVDGVEVHNAKTKPREEQYNSTYRVVSVLTVLHQDWLN*

*GKEYKCKVSNKALPAPIEKTISKAKGQPREPQVYTLPPSRDELTKNQVSL*

*TCLVKGFYPSDIAVEWESNGQPENNYKTTPPVLDSDGSFFLYSKLTVDKS*

*RWQQGNVFSCSVMHEALHNHYTQKSLSLSPGK*

Underlined portion represents extracellular domain of PD-1; Italic portion represents hFc (human IgG1).

Example 2. Purification of PD-L1, PD-1 Recombinant Protein, Hybridoma Antibody and Recombinant Antibody 1. Purification Steps of Recombinant Protein PD-L1 with His and PADRE Tag: PD-L1(ECD)-PADRE-His6 (SEQ ID NO: 2)

The supernatant sample, containing expressed cells, was centrifuged at high speed to remove impurities, the buffer was exchanged to PBS, and imidazole was added to a final concentration of 5 mM. A nickel column was equilibrated with PBS solution containing 5 mM imidazole and washed with 2-5 column volumes. After that, the supernatant sample was loaded onto the nickel column (GE, 17-5318-01). The column was washed with PBS solution containing 5 mM imidazole until the A280 reading returned to baseline. Then the column was washed with PBS plus 10 mM imidazole to remove nonspecific bound proteins and the effluent was collected. The target protein was eluted with PBS solution containing 300 mM imidazole and the elution peak was collected. The collected eluate was concentrated and further purified by chromatography gel Superdex200 (GE), the mobile phase was PBS. The mismatch peak was removed and the elution peak was collected. The obtained protein was identified by electrophoresis, peptide mapping (Agilent, 6530 Q-TOF), and LC-MS (Agilent 6530-TOF), and the correct sample was aliquoted for use. The PD-L1 protein with His and PADRE tag (PD-L1 (ECD)-PADRE-His6 E (SEQ ID NO: 2)) was obtained and used as an immunogen for the antibody of the present invention.

2. Purification Steps of Recombinant Protein PD-L1 with His and Flag Tag: PD-L1 (ECD)-Flag-His6 (SEQ ID NO: 3)

The sample was centrifuged at high speed to remove impurities and concentrated to an appropriate volume. The protein eluted from the IMAC column, as described above, was loaded onto a Flag affinity column (Sigma, A2220), which was equilibrated with 0.5×PBS and washed with 2-5 column volumes. The supernatant samples were loaded onto the column after removing impurities. The column was washed with 0.5×PBS until the A280 reading was reduced to baseline. Then, the column was washed with PBS containing 0.3 M NaCl, and the impurity protein was washed and collected. The target protein was eluted with 0.1 M acetic acid (pH 3.5-4.0) and collected, then the pH was adjusted to neutral. The collected eluate was concentrated and further purified by chromatography gel Superdex200 (GE), the mobile phase was PBS. The mismatch peak was removed and the elution peak was collected. The obtained protein was identified by electrophoresis, peptide mapping (Agilent, 6530 Q-TOF), and LC-MS (Agilent 6530-TOF), and the correct sample was aliquoted for use. The PD-L1 protein with His and Flag tag (PD-L1 (ECD)-Flag-His6 (SEQ ID NO: 3)) was obtained and used for performance testing of the antibodies in present invention.

3. Purification Steps of Fc Fusion Protein of PD-L1 and PD-1

The supernatant sample containing the expressed cells was centrifuged at high speed to remove impurities, concentrated to an appropriate volume, and then loaded onto a Protein A column (GE, 17-5438-01). The column was washed with 0.5×PBS until the A280 reading was reduced to baseline. The target protein was eluted with 100 mM sodium acetate (pH 3.0). 1M Tris™ HCl was used to neutralize the target protein. Then the neutralized protein was further purified by gel chromatography Superdex® 200 (GE), which was equilibrated with PBS. The mismatch peak was removed and the elution peak was collected, then the correct sample was aliquoted for use. This method was used to purify PD-L1 (ECD)-Fc (SEQ ID NO: 4) and PD-1 (ECD)-Fc (SEQ ID NO: 5). PD-1 (ECD)-Fc can be used as an antigen or detection reagent of the present invention and PD-1 (ECD)-Fc was used for performance testing of the antibody of the present invention.

Example 3. Preparation of Anti-humanPD-L1 Monoclonal Antibody

1. Immunization

The anti-human PD-L1 monoclonal antibody was produced by immunizing 6-week old female SJL white mice, (Beijing Vital River Laboratory Animal Technology Co., Ltd., animal production license number: SCXK (Beijing) 2012-0001).

Housing Environment: SPF level.

After the mice were purchased, the animals were kept in the laboratory for 1 week, 12/12 hours light/dark cycle, temperature 20-25° C., humidity 40-60%. After the mice had been acclimated to the environment, they were immunized according to two schemes (A and B), with 6-10 mice in each group. Immuno antigen was PD-L1 with His and PADRE tags ((PD-L1(ECD)-PADRE-His6 (SEQ ID NO: 2).

In Scheme A, Freund's adjuvant (sigma Lot Num: F5881/F5506) was for emulsification:

The first immunization was performed with Freund's complete adjuvant (CFA) and the other booster immunizations were performed with Freund's incomplete adjuvant (IFA). The ratio of antigen to adjuvant was 1:1, with dosing of 100 µg/mouse (first immunization) and 50 µg/mouse (booster immunization). On day 0, each mouse was intraperitoneal (IP) injected with 100 µg/mouse of the emulsified antigen, followed by immunization, once every two weeks for a total of 6-8 weeks.

In Scheme B, cross-immunization was performed alternatively with Titermax®: (sigma Lot Num: T2684) and Alum (Thremo Lot Num: 77161). The ratio of antigen to adjuvant (Titermax®) was 1:1 and the ratio of antigen to adjuvant (Alum) was 3:1, with dosing of 10-20 µg/mouse (first immunization) and 5 µg/mouse (booster immunization). On day 0, the mouse was intraperitoneal (IP) injected with 20 or 10 µg/mouse of the emulsified antigens, followed by immunization once a week. Titermax® and Alum were used alternately for a total 6-11 weeks. After four weeks of immunization, the antigen was administered via back or intraperitoneal injection, depending on the conditions of back lump and abdominal swelling.

2. Cell Fusion

Mice with higher serum antibody titers and the titers tending to plateau (See ELISA Test described in Test 1) were selected for splenocyte fusion. A shock immunization was performed by IP injection of 10 µg/mouse PD-L1-His 72 hours prior to splenocyte fusion. Hybridoma cells were obtained by fusing splenic lymphocytes with myeloma Sp2/0 cells (ATCC® CRL-8287™) using an optimized PEG-mediated fusion procedure. The hybridoma cells were resuspended in HAT complete medium (RPMI-1640 medium containing 20% FBS, 1×HAT and 1×OPI) and incubated in 96-well cell culture plates (1×10$^5$/150 µl/well) at 37° C., 5% CO$_2$. On day 5 after fusion, HAT complete medium was added to cells, 50 µl/well, and then incubated at 5% CO$_2$ and 37° C. Seven to eight days after fusion, according to the density of the growing cells, the whole medium was changed to HT complete medium (RPMI-1640 medium containing 20% FBS, 1×HT and 1×OPI), 200 µl/well, and then incubated at 5% CO$_2$ and 37° C.

3. Screening for Hybridoma Cell

On day 10-11 after fusion, an ELISA assay was performed on PD-L1 binding according to the density of the growing cells (see Test 1). For the positive cells detected in the ELISA assay (Test 1), blockade in PD-L1/PD-1 binding was detected via ELISA analysis (see Test 2). Medium in the positive wells was changed and the positive cells were expanded to a 24-well plate depending on cell density. After re-testing, the cells transferred into the 24-well plate were used for breed conservation and first sub-cloning. The positive cells during the first sub-clone screening (see Test 1) were used for breed conservation and subjected to a second sub-cloning. The positive cells during the second sub-cloning were (see Test 1) used for breed conservation and protein expression. Hybridoma cells having blocking effect on PD-L1 and PD-1 binding (see Test 2) were obtained by multiple cell fusions.

Hybridoma clones 9-2 and 24D5 were obtained by a blocking experiment and a binding experiment, the antibody was further prepared by ascites method or serum-free cell culture method, and then purified by purification steps indicated in the examples for use in the test.

The murine antibody heavy chain variable region sequence of hybridoma clone 9-2 is indicated as follows

```
>9-2 mVH: murine antibody heavy chain variable
region sequence of hybridoma clone 9-2
                                       SEQ ID NO: 6
EVQLQESGPGLAKPSQTLSLTCSVAGYSITNDYWNWIRKFPGNKLEYMGY
ISYTGSTYYNPSLKSRLSITRDTSKNQYYLQLNSVTAEDTAIYYCARSGG
WLAPFDYWGRGTTLTVSS >9-2 mVL: murine antibody light chain variable
region sequence of hybridoma clone 9-2
                                       SEQ ID NO: 7
DIVMSQSPSSLVVSVGEKVIMSCKSSQSLFYRSNQKNSLAWYQQKPGQSP
KLLIYGASTRESGVPDRFTGSGSGTDFTVTISSVKAEDLAVYYCQQYYGY
PYTFGGGTKLEIK
```

The order is FR1-CDR1-FR2-CDR2-FR3-CDR3-FR4, italic portion represents FR sequence, and underlined portion represents CDR sequence.

The murine antibody variable region sequence of hybridoma clone 24D5 is indicated as follows:

```
24D5-VH: murine antibody heavy chain variable
region sequence of hybridoma clone 24D5
                                       SEQ ID NO: 8
QVQLQQPGAELVKPGASVKLSCKASGYTFTSYWMHWVQQRPGQGLEWIGR
IHPNSGGTSYNEKFKNRATLTVDKSSSTAYMQFSSLTSEDSAVYYSARGG
SSYDYFDYWGQGTTLTVSS 24D5-VL: murine antibody light chain variable
region sequence of hybridoma clone 24D5
                                       SEQ ID NO: 9
DIVLTQSPASLAVSLGQRATISCRASESVSIHGTHLMHWYQQKPGQPPKL
LIYAASNLESGVPARFSGSGSETDFTLNIHPVEEEDATTYFCQQSFEDPL
TFGAGTKLELK
```

The order is FR1-CDR1-FR2-CDR2-FR3-CDR3-FR4, italic portion represents FR sequence, and the underlined portion represents CDR sequence.

Heavy and light chain CDR sequences are as follows:

|  |  | Heavy Chain |  | Light Chain |
|---|---|---|---|---|
| (9-2) | HCDR1 | NDYWN<br>SEQ ID NO: 38 | LCDR1 | KSSQSLFYRSNQKNSLA<br>SEQ ID NO: 40 |
|  | HCDR2 | YISYTGSTYYNPS<br>LKS<br>SEQ ID NO: 11 | LCDR2 | GASTRES<br>SEQ ID NO: 14 |
|  | HCDR3 | SGGWLAPFDY<br>SEQ ID NO: 12 | LCDR3 | QQYYGYPYT<br>SEQ ID NO: 15 |
| (24D5) | HCDR1 | SYWMH<br>SEQ ID NO: 16 | LCDR1 | RASESVSIHGTHLM<br>H<br>SEQ ID NO: 19 |
|  | HCDR2 | RIHPNSGGTSYNE<br>KFKN<br>SEQ ID NO: 39 | LCDR2 | AASNLES<br>SEQ ID NO: 20 |
|  | HCDR3 | GGSSYDYFDY<br>SEQ ID NO: 18 | LCDR3 | QQSFEDPLT<br>SEQ ID NO: 21 |

Wherein, when $X_1$ of SEQ ID NO: 10 is N, the sequence is SEQ ID NO: 38;
when $X_4$ of SEQ ID NO: 17 is H, $X_5$ of SEQ ID NO: 17 is G, the sequence is SEQ ID NO: 39;
when $X_2$ of SEQ ID NO: 13 is R, X3 of SEQID NO: 13 is N, the sequence is SEQ ID NO: 40.

Example 4. Humanization of Human Anti-PD-L1 Hybridoma Monoclonal Antibodies

1. Selection of Humanized Framework Sequences for Hybridoma Clone 9-2

After aligning with the IMGT human antibody heavy and light chain variable region gene database and MOE software, the heavy and light chain variable region genes with high homology to 9-2 and 24D5 were selected as templates, the CDRs of the two murine antibodies were grafted onto the corresponding human-derived template to form a variable region sequence in the order of FR1-CDR1-FR2-CDR2-FR3-CDR3-FR4. Wherein, amino acid residues were identified and annotated by the Kabat numbering system.

The humanized light chain template of the murine-derived antibody 9-2 is IGKV4-1*01 and hjk4.1, humanized heavy chain template is IGHV4-30-4*01 and hjh2, the sequence of humanized variable region is indicated as follows;

>9-2 hVH-CDR graft
SEQ ID NO: 22
QVQLQESGPGLVKPSQTLSLTCTVSGGSIS<u>NDYWN</u>WIRQHPGKGLEWIG<u>Y
ISYTGSTYYNPSLKS</u>RVTISVDTSKNQFSLKLSSVTAADTAVYYCAR<u>SGG
WLAPFDY</u>WGRGTLVTVSS >9-2 hVL CDR graft
SEQ ID NO: 23
DIVMTQSPDSLAVSLGERATINC<u>KSSQSLFYRSNQKNSLA</u>WYQQKPGQPP
KLLIY<u>GASTRES</u>GVPDRFSGSGSGTDFTLTISSLQAEDVAVYYC<u>QQYYGY
PYT</u>FGGGTKVEIK The order is FR1-CDR1-FR2-CDR2-FR3-CDR3-FR4, italic portion represents FR sequence, and the underlined portion represents CDR sequence.

2. Selection of a Template and Back-Mutation Design for Hybridoma Clone 9-2. See Table 1 as Below:

TABLE 1

| 9_2_VL | | 9_2_VH | |
|---|---|---|---|
| h9_2_VL.1 | Grafted | h9_2_VH.1 | Grafted |
| h9_2_VL.1A | P49S | h9_2_VH.1A | W47Y, V71R |
|  |  | h9_2_VH.1B | W47Y, V71R, G27Y, I48M, V67L |
|  |  | h9_2_VH.1C | W47Y, V71R, G27Y, I48M, V67L, F78Y, S30T |
|  |  | h9_2_VH.1D | W47Y, V71R, G27Y, I48M, V67L, F78Y, S30T, Q39K |

For example, P49S indicates a back-mutation from P to S at position 49 according to Kabat numbering system.

Grafted indicates that the murine antibody CDR was implanted into human germline FR sequences.

TABLE 2

| Humanized sequence combinations for murine antibody 9-2 | | | | | |
|---|---|---|---|---|---|
|  | h9_2_VH.1 | h9_2_VH.1A | h9_2_VH.1B | h9_2_VH.1C | h9_2_VH.1D |
| h9_2_VL.1 | 9_2-1 | 9_2-2 | 9_2-3 | 9_2-4 | 9_2-5 |
| h9_2_VL.1A | 9_2-6 | 9_2-7 | 9_2-8 | 9_2-9 | 9_2-10 |

This table shows various sequence combinations of different mutations. For example, 9_2-2 indicates that two mutations (light chain h9_2_VL1 and heavy chain h9_2-VH.1A) are present on the humanized murine antibody 9-2, and so on.

3. Selection of Humanized Framework for the Hybridoma Clone 24D5

A serine is located on position 96 of PD-L1 hybridoma monoclonal antibody 24D5, while a conserved cysteine is located on FR3 of the germline gene, from which an intrachain disulfide bond is formed with a cysteine at position 22. We constructed a 24D5 chimeric antibody and another chimeric antibody of 24D5 with a back-mutation from serine to cysteine at position 96. The affinities of the two forms of chimeric antibodies are consistent with the affinity of the hybridoma antibody. Humanization of the antibody was performed by CDR graft strategy, and since the mutation on position 96 of 24D5 occurred on the skeleton, it did not affect the design scheme.

The humanized light chain template for the murine-derived antibody 24D5 is IGKV7-3*01 and hjk2.1, humanized heavy chain template is IGHV1-46*01 and hjh6.1, the sequence of humanized variable region is indicated as follows:

```
>24D5 Humanized heavy chain variable region VH.1
                                    SEQ ID NO: 24
QVQLVQSGAEVKKPGASVKVSCKASGYTFTSYWMHWVRQAPGQGLEWMGR
IGPNSGGTSYNEKFKNRVTMTRDTSTSTVYMELSSLRSEDTAVYYCARGG
SSYDYFDYWGQGTTVTVSS >24D5 Humanized light chain variable region VL.1
                                    SEQ ID NO: 25
DIVLTQSPASLAVSPGQRATITCRASESVSIHGTHLMHWYQQKPGQPPKL
LIYAASNLESGVPARFSGSGSGTDFTLTINPVEANDTANYYCQQSFEDPL
TFGQGTKLEIK
```

The order is FR1-CDR1-FR2-CDR2-FR3-CDR3-FR4, italic portion represents FR sequence, and the underlined portion represents CDR sequence.

4. Selection of a Template and Back-Mutation Design for Hybridoma Clone 24D5. See Table 3 as Below:

TABLE 3

| 24D5_VL | | 24D5 _VH | |
|---|---|---|---|
| 24D5_VL.1 | Grafted | 24D5_VH.1 | Grafted |
| 24D5_VL.1A | Y91F | 24D5_VH.1A | T74K |
| 24D5_VL.1B | Y91F, G72E | 24D5_VH.1B | T74K, R72V, M48I, M70L |
| 24D5_VL.1C | Y91F, G72E, T22S | 24D5_VH.1C | T74K, R72V, M48I, M70L, R38Q |
| | | 24D5_VH.1D | T74K, R72V, M48I, M70L, R38Q, L83F |
| | | 24D5_VH.1E | T74K, R72V, M48I, M70L, R38Q, L83F, V68A, V79A |

For example, Y91F indicates a back-mutation from Y to F at position 91 according to Kabat numbering system.

Grafted indicates that the murine antibody CDR was implanted into human germline FR sequences.

TABLE 4

| Humanized sequence combinations for murine antibody 24D5 | | | | |
|---|---|---|---|---|
| | h24D5_VL.1 | h24D5_VL.1A | h24D5_VL.1B | h24D5_VL.1C |
| h24D5_VH.1 | 1 | 2 | 3 | 4 |
| h24D5_VH.1A | 5 | 6 | 7 | 8 |
| h24D5_VH.1B | 9 | 10 | 11 | 12 |
| h24D5_VH.1C | 13 | 14 | 15 | 16 |
| h24D5_VH.1D | 17 | 18 | 19 | 20 |
| h24D5_VH.1E | 21 | 22 | 23 | 24 |

This table shows various sequence combinations of different mutations. For example, 5 indicates that two kinds of mutation (heavy chain h24D5_VH.1A and light chain h24D5_VL.1) are present on the humanized murine antibody 5, and so on.

Example 5. Construction of Humanized Clone

Primers were designed and VH/VK gene fragments of each humanized antibody were constructed by PCR and then inserted into the expression vector pHr (with signal peptide and constant region gene (CH1-FC/CL) fragment) via homologous recombination, to construct a full length of the antibody expression vector: VH-CH1-FC-pHr/VK-CL-pHr.

1. Primer Design:

The online software DNAWorks (v3.2.2) (http://helixweb.nih.gov/dnaworks/) was used to design multiple primers for synthesis of VH/VK gene fragments required for recombination: 5'-30 bp signal peptide+VH/VK+30 bp CH1/CL-3'. Rules for primer design: If there are two different amino acids between target gene 2 and the target gene 1, another primer comprising the mutation site was designed, as shown in FIG. 1.

2. Fragment Splicing:

According to operating instructions for DNA polymerase from TaKaRa Company PrimeSTAR® GXL, using the primers designed above, VH/VK gene fragment containing the recombinant gene required was amplified by two-step PCR.

Figure 2:
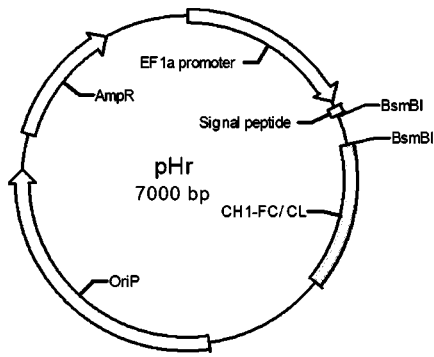
FIG. 2: Schematic diagram of vectors for constructing a humanized clone

3. Construction of Expression Vector pHr (With Signal Peptide and Constant Region Gene (CH1-FC/L) Fragment) and Enzyme Digestion:

The expression vector pHr (with signal peptide and constant region gene (CH1-FC/CL) fragment) was designed and constructed by using some special restriction endonuclease, such as BsmBI, whose recognition sequence is different from the restriction site, as shown in FIG. 2. BsmBI digested the vector, then digested fragments were gel extracted and stored for use.

4. Recombinant Construction of Expression Vector VH-CH1-FC-pHr/VK-CL-pHr

VH/VK containing gene fragments required for recombinant and expression vector pHr (with signal peptide and constant region gene (CH1-FC/CL) fragment) that had been digested with BsmBI were added into DH5H competent cells at a ratio of 3:1, incubated at 0° C. on ice for 30 min, heat-shocked at 42° C. for 90 s, combined with 5 volumes of LB medium, incubated at 37° C. for 45 min, coated on LB-Amp plate, and cultured at 37° C. overnight. A single clone was picked for sequencing and a clone of interest was obtained.

5. The plasmid was constructed according to the design of the present example, then the purified protein was expressed according to Example 2, and the affinity of the obtained protein was measured by the detection Example SPR.

6. Result:

The affinity of 9_2-2 was measured by BIACORE™ (Test 4), which was similar to the chimeric antibody, and only a slight increase in affinity was observed with more back-mutations. A good affinity was obtained by directly embedding the CDRs of antibody 24D5 into the humanized template, but the affinity of chimeric antibody itself was weaker than the hybridoma antibody. Introduction of N85E into the light chain for deglycosylation can improve homogeneity of the product and did not affect the affinity.

Finally, BIACORE™ was used to test the affinity of humanized variant having back-mutations to human PD-L1-his or hybridoma antibody, the humanized back-mutation sites and sequence combinations were selected as shown in Table 5:

TABLE 5

| Humanized variants | VH | VL | Kd (Humanized) | Kd (Hybridoma) |
|---|---|---|---|---|
| 9_2-2 | VH.1 W47Y/V71R | VL.1 | 5.68E-10 | 4.79E-10 |
| 24D5-H | CDR Graft | VL.1 N85E | 1.68E-10 | 6.68E-11 |

Example 6. Affinity Maturation of the Humanized Anti-PD-L1 Antibody

1. Construction of Humanized 9-2-2 and 24D5 Phagemid Vectors

The humanized 9-2-2 and 24D5 were constructed into the phagemid vector in scFv mode ((VH-3(GGGGS(SEQ ID NO: 41))-VL)) respectively, as a wild-type sequence (i.e., as an original or initial sequence relative to the mutant sequence obtained from the affinity maturation screening). Using overlap PCR, VH, 3 linkers (GGGGS(SEQ ID NO: 41), and VL were spliced and then ligated into the phagemid vector via NcoI and NotI cleavage sites.

2. Construction of Phage Display Library

The mutant library was constructed by using constructed wild-type scFv as template and codon-based primers. In the process of primer synthesis, each codon in the mutant region had 50% wild-type codons and a NNK of 50% (MNN for reverse primer), which was introduced into all CDR regions. The PCR fragment was digested with NcoI and NotI, ligated into the phagemid vector, and finally electrically transformed into *E. coli* TG1. Each codon-based primer was established as an independent library, in which 9-2-2 was divided into 7 libraries and 24D5 was divided into 8 libraries.

3. Library Panning

The biotinylated human PD-L1 (ECD) antigen and streptavidin magnetic beads were used for liquid-phase panning, and in each round of screening the antigen concentration was reduced relative to the previous round, after packaging phage particles used in the screening through the rescue of the library. After three rounds of panning, 250 clones of 9-2-2 and 24D5 antibodies were picked respectively, then subjected to phage ELISA to detect the binding activity, and the positive clones were sequenced.

4. Surface Plasmon Resonance (SPR) for Detection of Affinity

After the sequence analysis on the sequencing clones, the non-redundant sequences were transformed into full-length IG (γ1, κ) for mammalian cell expression after removal of the redundant sequence. The full length IG after affinity purification was determined by BIAcore™ X-100 instrument (GE Life Sciences) for affinity assay.

Confirmed the selected variable region sequence:

```
>9-2 hVH(T)
                                     SEQ ID NO: 26
QVQLQESGPGLVKPSQTLSLTCTVSGGSISNDYWTWIRQHPGKGLEYIGY
ISYTGSTYYNPSLKSRVTISRDTSKNQFSLKLSSVTAADTAVYYCARSGG
WLAPFDYWGRGTLVTVSS
```

Wherein, CDR1 is SEQ ID NO: 10 when $X_1$ is T.

```
>9-2 hVL(H)
                                     SEQ ID NO: 27
DIVMTQSPDSLAVSLGERATINCKSSQSLFYHSNQKHSLAWYQQKPGQP
PKLLIYGASTRESGVPDRFSGSGSGTDFTLTISSLQAEDVAVYYCQQYY
GYPYTFGGGTKVEIK
```

Wherein, CDR1 is SEQ ID NO: 13 when $X_2$ is H and $X_3$ is H.

Affinity Maturation:

```
>24-D5 hVH(GF)
                                     SEQ ID NO: 28
QVQLVQSGAEVKKPGASVKVSCKASGYTFTSYWMHWVRQAPGQGLEWMG
RIGPNSGFTSYNEKFKNRVTMTRDTSTSTVYMELSSLRSEDTAVYYCAR
GGSSYDYFDYWGQGTTVTVSS
```

Wherein, CDR2 is SEQ ID NO: 17 when $X_4$ is G and $X_5$ is F.

```
>24-D5 hVL
                                     SEQ ID NO: 29
DIVLTQSPASLAVSPGQRATITCRASESVSIHGTHLMHWYQQKPGQPP
KLLIYAASNLESGVPARFSGSGSGTDFTLTINPVEAEDTANYYCQQSF
EDPLTFGQGTKLEIK
```

The order is FR1-CDR1-FR2-CDR2-FR3-CDR3-FR4, italic portion represents FR sequence, and the underlined portion represents CDR sequence, wherein the double underlined sites were obtained by affinity maturation after screening.

Example 7. Construction and Expression of Anti-PD-L1 Human IgG4 Type

Since PD-L1 is also expressed in activated T cells, the use of wild-type IgG1 constant regions will induce Fc-mediated effects, such as ADCC and CDC, leading to reduction in the activated T cells. Mutations in the IgG1 Fc such as D265A, N297A, L234A/L235A or L234F/L235A can reduce ADCC, and P331S or mutations near the position 331 can reduce CDC. Mutation of IgG2 and IgG2/4 Fc hybridization antibodies can also reduce ADCC and CDC effects. Mutant IgG4 was selected herein to obtain antibodies without ADCC and CDC. Thus, the clones obtained by affinity maturation were converted to IgG4 type, and the core hinge region of IgG4 contains the S228P mutation, which strengthens the linking of the disulfide bond in the core hinge region, thereby preventing the exchange of IgG4 Fab arms and greatly reducing the formation of hemi-molecule antibodies. F234A and L235A mutations (mAbs 4: 3, 310-318; May/June 2012) were further introduced. This form of IgG4 mutant antibody changes the CH2 domain and reduces the interaction with Fc receptors to achieve the effect of reducing ADCC activity. The purified 9-2 H2L10 antibody was expressed according to the present example and named HRP00049, and the expressed 24D5 29H1 GF was named HRP00052. These proteins will be further identified in the test case.

The affinity test for the IgG4 type mutant with the human PD-L1-his or rhesus monkey PD-L1-his is shown in Test 4, Table 6.

```
HRP00049: 9-2(H2/L10) IgG4 (AA)(S228P)
Heavy chain: Heavy chain sequence of HRP00049
antibody
                                     SEQ ID NO: 30
QVQLQESGPGLVKPSQTLSLTCTVSGGSISNDYWTWIRQHPGKGLEYIG

YISYTGSTYYNPSLKSRVTISRDTSKNQFSLKLSSVTAADTAVYYCARS

GGWLAPFDYWGRGTLVTVSSASTKGPSVFPLAPCSRSTSESTAALGCLV
```

-continued

KDYFPEPVTVSWNSGALTSGVHTFPAVLQSSGLYSLSSVVTVPSSSLGT

KTYTCNVDHKPSNTKVDKRVESKYGPPCPPCPAPEAAGGPSVFLFPPKP

KDTLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTT

PPVLDSDGSFFLYSRLTVDKSRWQEGNVFSCSVMHEALHNHYTQKSLSL

SLGK

Gene sequence encoding HRP00049 antibody heavy chain:
SEQ ID NO: 31
CAGGTGCAACTGCAGGAGAGCGGCCCCGGACTCGTGAAACCCTCCCAGA

CCCTGAGCCTGACCTGTACCGTGAGCGGCGGCAGCATCAGCAACGACTA

CTGGACTTGGATCAGGCAGCACCCCGGCAAAGGCCTGGAGTACATCGGC

TACATCAGCTACACCGGCTCCACCTACTACAACCCCAGCCTGAAGTCCA

GGGTGACCATCAGCCGGGACACCAGCAAGAACCAGTTCAGCCTGAAGCT

GAGCAGCGTGACCGCTGCCGACACAGCCGTGTACTATTGTGCCAGAAGC

GGCGGATGGCTGGCCCCTTTCGACTACTGGGGCAGAGGCACCCTGGTGA

CCGTGAGCAGCGCTTCCACCAAGGGCCCATCGGTCTTCCCCCTGGCGCC

CTGCTCCAGGAGCACCTCCGAGAGCACAGCCGCCCTGGGCTGCCTGGTC

AAGGACTACTTCCCCGAACCGGTGACGGTGTCGTGGAACTCAGGCGCCC

TGACCAGCGGCGTGCACACCTTCCCGGCTGTCCTACAGTCCTCAGGACT

CTACTCCCTCAGCAGCGTGGTGACCGTGCCCTCCAGCAGCTTGGGCACG

AAGACCTACACCTGCAACGTAGATCACAAGCCCAGCAACACCAAGGTGG

ACAAGAGAGTTGAGTCCAAATATGGTCCCCCATGCCCACCATGCCCAGC

ACCTGAGGCTGCTGGGGACCATCAGTCTTCCTGTTCCCCCCAAAACCC

AAGGACACTCTCATGATCTCCCGGACCCCTGAGGTCACGTGCGTGGTGG

TGGACGTGAGCCAGGAAGACCCCGAGGTCCAGTTCAACTGGTACGTGGA

TGGCGTGGAGGTGCATAATGCCAAGACAAAGCCGCGGGAGGAGCAGTTC

AACAGCACGTACCGTGTGGTCAGCGTCCTCACCGTCCTGCACCAGGACT

GGCTGAACGGCAAGGAGTACAAGTGCAAGGTCTCCAACAAAGGCCTCCC

GTCCTCCATCGAGAAAACCATCTCCAAAGCCAAAGGGCAGCCCCGAGAG

CCACAGGTGTACACCCTGCCCCCATCCCAGGAGGAGATGACCAAGAACC

AGGTCAGCCTGACCTGCCTGGTCAAAGGCTTCTACCCCAGCGACATCGC

CGTGGAGTGGGAGAGCAATGGGCAGCCGGAGAACAACTACAAGACCACG

CCTCCCGTGCTGGACTCCGACGGCTCCTTCTTCCTCTACAGCAGGCTCA

CCGTGGACAAGAGCAGGTGGCAGGAGGGGAATGTCTTCTCATGCTCCGT

GATGCATGAGGCTCTGCACAACCACTACACACAGAAGAGCCTCTCCCTG

TCTCTGGGTAAATGA

Light chain: Light chain sequence of HRP00049 antibody
SEQ ID NO: 32
DIVMTQSPDSLAVSLGERATINCKSSQSLFYHSNQKHSLAWYQQKPGQP

PKLLIYGASTRESGVPDRFSGSGSGTDFTLTISSLQAEDVAVYYCQQYY

GYPYTFGGGTKVEIKRTVAAPSVFIFPPSDEQLKSGTASVVCLLNNFYP

REAKVQWKVDNALQSGNSQESVTEQDSKDSTYSLSSTLTLSKADYEKHK

VYACEVTHQGLSSPVTKSFNRGEC

Gene sequence encoding HRP00049 antibody light chain:
SEQ ID NO: 33
GACATCGTGATGACCCAGAGCCCTGATAGCCTGGCTGTGAGCCTGGGC

GAGAGAGCCACCATCAACTGCAAGAGCAGCCAGAGCCTGTTCTACCAT

AGCAACCAGAAGCACAGCCTCGCCTGGTATCAGCAGAAGCCCGGCCAA

CCCCCCAAGCTGCTGATCTACGGCGCCAGCACAAGAGAGAGCGGAGTG

CCCGATAGGTTCAGCGGCAGCGGATCCGGCACCGATTTCACCCTGACC

ATCAGCAGCCTGCAGGCCGAGGATGTGGCCGTGTACTACTGCCAGCAG

TACTACGGCTACCCTTACACCTTCGGCGGCGGCACCAAGGTGGAGATC

AAGCGTACGGTGGCTGCACCATCTGTCTTCATCTTCCCGCCATCTGAT

GAGCAGTTGAAATCTGGAACTGCCTCTGTTGTGTGCCTGCTGAATAAC

TTCTATCCCAGAGAGGCCAAAGTACAGTGGAAGGTGGATAACGCCCTC

CAATCGGGTAACTCCCAGGAGAGTGTCACAGAGCAGGACAGCAAGGAC

AGCACCTACAGCCTCAGCAGCACCCTGACGCTGAGCAAAGCAGACTAC

GAGAAACACAAAGTCTACGCCTGCGAAGTCACCCATCAGGGCCTGAGC

TCGCCCGTCACAAAGAGCTTCAACAGGGGAGAGTGTTGA

HRP00052: 24D5(GF) IgG4 (AA) (S228P)
Heavy chain: Heavy chain sequence of HRP00052 antibody
SEQ ID NO: 34
QVQLVQSGAEVKKPGASVKVSCKASGYTFTSYWMHWVRQAPGQGLEWM

GRIGPNSGFTSYNEKFKNRVTMTRDTSTSTVYMELSSLRSEDTAVYYC

ARGGSSYDYFDYWGQGTTVTVSSASTKGPSVFPLAPCSRSTSESTAAL

GCLVKDYFPEPVTVSWNSGALTSGVHTFPAVLQSSGLYSLSSVVTVPS

SSLGTKTYTCNVDHKPSNTKVDKRVESKYGPPCPPCPAPEAAGGPSVF

LFPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNG

QPENNYKTTPPVLDSDGSFFLYSRLTVDKSRWQEGNVFSCSVMHEALH

NHYTQKSLSLSLGK

Gene sequence encoding HRP00052 antibody heavy chain:
SEQ ID NO: 35
CAGGTGCAACTGGTGCAGAGCGGTGCCGAGGTGAAGAAGCCTGGCGCA

AGCGTGAAAGTGAGCTGCAAGGCCAGCGGCTACACCTTCACCAGCTAC

TGGATGCACTGGGTGAGGCAGGCCCCTGGACAGGGCCTGGAGTGGATG

GGCAGGATCGGGCCCAACAGTGGTTTCACTAGCTACAATGAAAAGTTC

AAGAACAGGGTAACCATGACCAGGGACACCTCCACCAGCACAGTGTAT

ATGGAGCTGAGCAGCCTGAGGAGCGAGGACACCGCCGTGTACTACTGT

GCCAGAGGCGGCAGCAGCTACGACTACTTCGACTATTGGGGCCAGGGC

ACCACCGTGACCGTGAGCAGTGCTTCCACCAAGGGCCCATCGGTCTTC

CCCCTGGCGCCCTGCTCCAGGAGCACCTCCGAGAGCACAGCCGCCCTG

```
GGCTGCCTGGTCAAGGACTACTTCCCCGAACCGGTGACGGTGTCGTGG

AACTCAGGCGCCCTGACCAGCGGCGTGCACACCTTCCCGGCTGTCCTA

CAGTCCTCAGGACTCTACTCCCTCAGCAGCGTGGTGACCGTGCCCTCC

AGCAGCTTGGGCACGAAGACCTACACCTGCAACGTAGATCACAAGCCC

AGCAACACCAAGGTGGACAAGAGAGTTGAGTCCAAATATGGTCCCCCA

TGCCCACCATGCCCAGCACCTGAGGCTGCTGGGGGACCATCAGTCTTC

CTGTTCCCCCCAAAACCCAAGGACACTCTCATGATCTCCCGGACCCCT

GAGGTCACGTGCGTGGTGGTGGACGTGAGCCAGGAAGACCCCGAGGTC

CAGTTCAACTGGTACGTGGATGGCGTGGAGGTGCATAATGCCAAGACA

AAGCCGCGGGAGGAGCAGTTCAACAGCACGTACCGTGTGGTCAGCGTC

CTCACCGTCCTGCACCAGGACTGGCTGAACGGCAAGGAGTACAAGTGC

AAGGTCTCCAACAAAGGCCTCCCGTCCTCCATCGAGAAAACCATCTCC

AAAGCCAAAGGGCAGCCCCGAGAGCCACAGGTGTACACCCTGCCCCCA

TCCCAGGAGGAGATGACCAAGAACCAGGTCAGCCTGACCTGCCTGGTC

AAAGGCTTCTACCCCAGCGACATCGCCGTGGAGTGGGAGAGCAATGGG

CAGCCGGAGAACAACTACAAGACCACGCCTCCCGTGCTGGACTCCGAC

GGCTCCTTCTTCCTCTACAGCAGGCTCACCGTGGACAAGAGCAGGTGG

CAGGAGGGGAATGTCTTCTCATGCTCCGTGATGCATGAGGCTCTGCAC

AACCACTACACACAGAAGAGCCTCTCCCTGTCTCTGGGTAAATGA

Light chain: Light chain sequence of HRP00052
antibody
                                           SEQ ID NO: 36
DIVLTQSPASLAVSPGQRATITCRASESVSIHGTHLMHWYQQKPGQPP

KLLIYAASNLESGVPARFSGSGSGTDFTLTINPVEAEDTANYYCQQSF

EDPLTFGQGTKLEIKRTVAAPSVFIFPPSDEQLKSGTASVVCLLNNFY

PREAKVQWKVDNALQSGNSQESVTEQDSKDSTYSLSSTLTLSKADYEK

HKVYACEVTHQGLSSPVTKSFNRGEC

Gene sequence encoding HRP00052 antibody light
chain:
                                           SEQ ID NO: 37
GACATCGTGCTGACCCAGAGTCCCGCCTCACTTGCCGTGAGCCCCGGT

CAGAGGGCCACCATCACCTGTAGGGCCAGCGAGAGCGTGAGCATCCAC

GGCACCCACCTGATGCACTGGTATCAACAGAAACCCGGCCAGCCCCCC

AAACTGCTGATCTACGCCGCCAGCAACCTGGAGAGCGGCGTGCCCGCC

AGGTTCAGCGGCTCCGGCAGCGGCACCGACTTCACCCTCACTATCAAC

CCCGTGGAGGCCGAGGACACCGCCAACTACTACTGCCAGCAGAGCTTC

GAGGACCCCCTGACCTTCGGCCAGGGCACCAAGCTGGAGATCAAGCGT

ACGGTGGCTGCACCATCTGTCTTCATCTTCCCGCCATCTGATGAGCAG

TTGAAATCTGGAACTGCCTCTGTTGTGTGCCTGCTGAATAACTTCTAT

CCCAGAGAGGCCAAAGTACAGTGGAAGGTGGATAACGCCCTCCAATCG

GGTAACTCCCAGGAGAGTGTCACAGAGCAGGACAGCAAGGACAGCACC

TACAGCCTCAGCAGCACCCTGACGCTGAGCAAAGCAGACTACGAGAAA

CACAAAGTCTACGCCTGCGAAGTCACCCATCAGGGCCTGAGCTCGCCC

GTCACAAAGAGCTTCAACAGGGGAGAGTGTTGA
```

The underlined portion is a nucleotide sequence encoding a variable region sequence of the antibody heavy or light chain. The non-underlined portion is a nucleotide sequence encoding an antibody constant region sequence.

The performance and benefits of the present invention are verified by biochemical tests as indicated below.

Test 1. Binding ELISA for PD-L1

Microtitration plates were directly coated with 1 μg/ml (100 μg/well) of PD-L1(ECD)-Fc (SEQ ID NO: 4) and incubated at 4° C. overnight. Then the plates were blocked with 150 μl/well of PBS containing 5% Skim Milk (BD, 232100) and incubated at 4° C. overnight. The plates were then washed twice, 50 μl/well of cell supernatant was added to each well, and the plates were incubated at 37° C. for 2 h. The plates were washed three times, 50 μl/well of Peroxidase-AffiniPure Goat Anti-Human IgG (Jackson, 115-035-003) which was diluted with KPL Milk (KPL, 50-82-01) at a ratio of 1:5000 was added to each well, and the plates were incubated at 37° C. for 1 h. Next, the plates were washed four times, 50 μl/well of TMB was added to each well, and the plates were incubated at 37° C. for 10 min. The reaction was stopped by the addition of 50 μl/well of 1M $H_2SO_4$ to each well and the OD value was read on an ELISA microplate reader (BMG Labtech, NOVOStar) at a wavelength of 450 nm.

Test 2. Blocking ELISA Assay for the Binding Between PD-L1 and PD-1

The dilution of biotin (Dojindo Chemical, LK03: 3 samples) and avidin (Sigma. S2438-250UG) was 6% BSA (diluted with PBS containing 0.1% Tween®20), and PBS was used as coating solution. Microtitration plates were directly coated with 1 μg/ml (100 μg/well) of PD-L1(ECD)-Fc (SEQ ID NO: 4) and incubated at 4° C. overnight. The plate was washed three times and was blocked for 2 h at 37° C. with 3% BSA (diluted with PBS containing 0.1% Tween®20). The plate was washed three times and 50 μl/well of cell supernatant was added to each well. Then 50 μl/well of bio-PD-1-Fc (biotin-labeled PD-1-Fc, SEQ ID NO: 5, 2 μg/ml, PD-1-FC was labeled according to the method of Dojindo Chemical Kits Biotin Labeling Kit-NH2, LK03: 3 samples) was added to each well, well-mixed by vortex, and incubated at 37° C. for 1 h. The plates were washed 6 times, followed by addition of 50 μl/well Streptavidin-Peroxidase Polymer (S2438-250UG, Sigma, which was diluted at a ratio of 1:400), and incubated on shaker for 50 min at room temperature. The plate was washed 6 times, and then 100 μl/well of TMB was added, and incubated for 5-10 min at 37° C. Then the reaction was terminated with addition of 100 μl/well of 1M $H_2SO_4$. The absorbance value was read on microplate reader (BMG Labtech, NOVOStar) at 450 nm, and the $IC_{50}$ value for blocking the binding of PD-1 antibody to ligand PD-L1 was calculated. The blocking activity of the humanized antibody of the present invention in PD-L1/PD-1 binding is shown in Table 6 below.

A similar single point blocking assay was also used to screen hybridoma antibodies.

Test 3. Blockade in PD-L1 and B7.1 Binding by PD-L1 Antibody

This assay was similar to the blocking assay (Test 2) of PD-L1 antibody on the binding between PD-L1 and PD-1. Bio-human PD-1 (ECD) –FC in Test 2 was replaced with bio-human-B7.1 (human-B7.1, Sino Biological 10698-H03H-200), and the other steps were the same. In addition, we also detected the specific blockade of PD-L1 antibody in hybridoma antibodies and humanized antibodies has been summarized in other examples. Table 7 below shows the affinities of the antibodies subjected to affinity maturation and the control antibody to human PD-L1 antigen (huPD-L1-his, Sino biological, 10084-H08H-200), cynomolgus PD-L1 antigen (Cyno PD-L1-his, Sino (90251-C08H-100) and murine PD-L1 antigen (Mouse PD-L1-his, Sino biological, 50010-M08H-100).

TABLE 7

Dissociation constants and species selectivity of HRP00049 and HRP00052

| | huPD-L1-his | | | CynoPD-L1-his | | | mousePD-L1 | | |
|---|---|---|---|---|---|---|---|---|---|
| Antibody | ka (1/Ms) | kd (1/s) | KD (M) | ka (1/Ms) | kd (1/s) | KD (M) | ka (1/Ms) | kd (1/s) | KD (M) |
| HRP00052 | 1.77E+06 | 1.01E−04 | 5.70E−11 | 1.84E+06 | 1.06E−04 | 5.79E−11 | NA | NA | NA |
| HRP00049 | 9.52E+05 | 1.62E−04 | 1.70E−10 | 9.74E+05 | 1.67E−04 | 1.72E−10 | NA | NA | NA |
| MPDL3280A | 1.15E+06 | 2.79E−04 | 2.43E−10 | | | 5.63E−09 | 3.48E+05 | 1.24E−03 | 3.56E−09 |

PD-L2-Fc (Q9BQ51, extracellular domain (aa20-aa220)) and PD-1 antibody binding similarly, and found that the antibody to be tested did not block the binding between PD-L2 and PD-1.

A similar single point blocking assay was used to screen hybridoma antibodies.

The blocking activity of humanized antibody of the present invention for PD-L1 and B7.1 binding and PD-L2 and PD-1 binding in are shown in Table 6 below.

TABLE 6

The blocking activity of the humanized antibody of the present invention

| Antibody to be tested | huPD-L1-Fc/ huPD-1 binding IC50 (ng/ml) | huPD-LI-Fc/ huB7.1-Fc binding IC50 (ng/ml) | huPD-L2-Fc/ huPD-1 binding IC50 (ng/ml) |
|---|---|---|---|
| HRP00052 | 114 | 69.6 | NA |
| HRP00049 | 174 | 113 | NA |
| MPDL3280A | 126 | 92.9 | NA |

NA indicates no blocking activity.

Test 4. Determination of the Affinity of PD-L1 Antibody HRP00049 and HRP00052 to PD-L1 Antigen by Biacore™ Assay The anti-human capture antibody was covalently linked to the CM5 biochip (GE, BR-1000-12) according to the method described in the anti-human trapping kit (GE, BR-1008-39) instructions for affinity capturing the PD-L1 antibody of the present invention. Then, a series of concentrations of human PD-L1 antigen (Sino biological, 10084-H08H-200) were flowed through the surface of the biochip, and the reaction signal was detected in real time using a Biacore™ instrument (GE. Biacore™X100) to obtain the association and dissociation curves. Finally, the affinity values were obtained by fitting. After each cycle of dissociation was finished in the experiment, the biochip was washed and regenerated with regeneration solution in the anti-human capture kit (GE). The data obtained was analyzed by GE's BIA evaluation software using a 1:1 (Langmuir) binding model. Ka (kon), kd (koff) and KD values were determined by the assay. The affinity of Test 5. In Vitro Cytology Test Fresh human peripheral blood mononuclear cell (PBMC) proliferation assay affected by the antibody was performed to detect the cell activity with respect to the PD-L1 antibody.

Fresh human PBMCs (randomly collected from healthy persons) were adjusted to density of $2 \times 10^6$/mL, inoculated in a 6-well plate at 2 ml/well, and incubated for 6 hours at 37° C., 5% $CO_2$. After the suspended cells were discarded, each well of adherent cells was mixed with 2 ml of RPMI1640 medium containing 100 ng/ml GM-CSF (granulocyte colony stimulating biological factor, Peprotech, AF-300-03) and 100 ng/ml IL-4 (Peprotech, AF-200-04). Two days after incubation, another 1 ml of RPMI1640 medium containing 100 ng/ml GM-CSF and 100 ng/ml IL-4 was added, then the cells were continually cultured for 2 days, followed by addition of 100 ng/ml TNF-α (tumor necrosis factor-α, Peprotech, AF-300-01 A) into each well, and cells were cultured for another 2 days to obtain mature dendritic cells. The dendritic cells and allogeneic T cells were centrifuged and resuspended at a concentration of $1 \times 10^6$/ml and $1 \times 10^5$/ml, respectively, and pipetted into a 96-well plate at 100 μl/well, followed by addition of 20 μl/well of antibody which was serially diluted into different concentrations with PBS, and then the cells were cultured in the incubator at 37° C., 5% $CO_2$ for 5 days. Thereafter, 100 μl was sampled for the detection of cell proliferation with CellTiter-Glo® Luminescent Cell Viability Assay kit. At the same time, the secretion of cytokine IFN-γ (interferon-γ) was determined.

Figure 3:
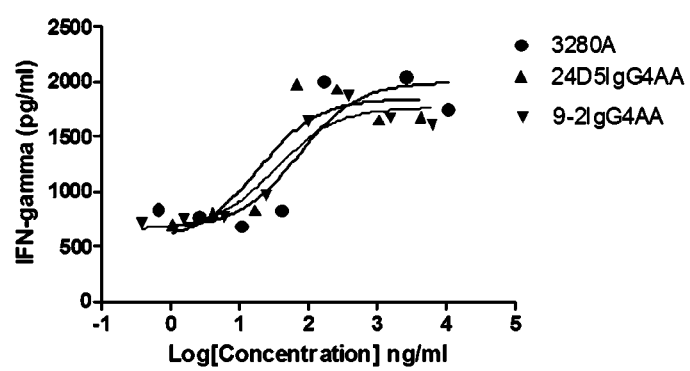
FIG. 3: Stimulation of PBMC proliferation by a humanized antibody

Both HRP00052 and HRP00049 can effectively stimulate the secretion of cytokine IFN-γ. The same method was also used to detect the stimulation on PBMC proliferation (FIG. 3) and on the secretion of cytokine IFN-γ (Table 8) by humanized antibody. From FIG. 3 and Table 8, it was found that the humanized antibody of the present invention was more effective in stimulating the proliferation of PBMC and the secretion of cytokine IFN-γ than the positive control MPDL3280A (Atezolizumab, WHO Drug Information, Vol. 28, No. 4, 2014, P488).

TABLE 8

Both HRP00052 and HRP00049 stimulate PBMC to release cytokines IFN-γ

| antibody to be tested | EC50 for cytokines IFN-γ release(ng/ml) |
|---|---|
| MPDL3280A | 72.1 |
| HRP00052 | 18.7 |
| HRP00049 | 34 |

Test 6. Activity of Antibody on Tuberculin-Stimulated PBMC Proliferation

The activity of the test antibody HRP00052, HRP00049 and reference antibody on tuberculin-stimulated PBMC proliferation in vitro was determined.

15 ml of fresh PBMCs, about $3 \times 10^7$, were added into 20 μl tuberculin (Shanghai Biyou Biotechnology, cat #97-8800) and the mixture was incubated in the incubator for 5 days at the 37° C., 5% $CO_2$. On day 6, the cultured cells were centrifuged and resuspended into fresh medium with the density adjusted to $5 \times 10^5$ cells/ml. 190 μl of resuspended cells were added into a 96-well plate, 10 μl/well of humanized antibody HRP00052 or HRP00049 was added into the corresponding well of the 96-well cell culture plate and 10 μl PBS was added in the control and blank group, respectively. Then, the cell culture plate was incubated in the incubator at the 37° C., 5% $CO_2$, and 72 hours later, PBMC proliferation (Promega, cat #G7571) and IFN-γ secretion (Neo Bioscience, cat #EHC102g) were determined. The results are shown in Table 9 below.

TABLE 9

Activity of the humanized antibody on tuberculin-stimulated PBMC proliferation

| Antibody to be tested | $EC_{50}$(ng/ml) for T cell proliferation | $EC_{50}$(ng/ml) for IFN-γ |
|---|---|---|
| HRP00052 | 9.8 | 19.6 |
| HRP00049 | 112 | 45.5 |
| MPDL3280A | 1464 | 353 |

Result: This experiment demonstrates that the humanized antibodies of the present invention have a stronger stimulating effect on PBMC proliferation which has previously been stimulated by exogenous antigen, and the characteristic has an unexpected effect when applied to the tumor treatment.

Test 7. Inhibitory Effect of PD-L1 Antibody HRP00052 on the Tumor Cell Growth in Mice Bearing U87MG Tumor In this study, human glioblastoma U87MG cells were inoculated into the immunodeficient mice. After the tumor was formed, human PBMCs activated by anti-CD3 antibody were injected into tumor tissue to evaluate the effect of PD-L1 antibody in the treatment of mice subcutaneously injected with glioblastoma U87 MG tumor.

PBMCs were isolated from the blood provided by two volunteers, cultured and activated by anti-CD3 antibody (Miltenyi Biotec, 130-093-387). U87MG cells were inoculated subcutaneously in right ribs of SCID mice (Vital River 11400700081219), two weeks later, as the volume of tumor was ≥40 $mm^3$, the mice with too large or too small body weight or tumor size were discarded. The remaining mice were randomly divided into groups according to the tumor volume. The two volunteer-derived PBMCs were stimulated with CD3 antibody, then were mixed at a ratio 1:1 and injected into the tumor tissue. Meanwhile, the subcutaneous injection of antibody or blank vector (5% glucose solution) was initiated. Administration was performed once on day 0, 7, 14 and 21, respectively, totally 4 times.

The result is shown in Table 10, indicating that the 3 mg/kg dose of PD-L1 antibody HRP00052 could significantly inhibit the growth of subcutaneous tumor of human malignant glioma U87MG.

TABLE 10

Effect of PD-L1 antibody on the treatment of mice subcutaneously grafted with glioma U87MG

| Group | Day 0 Mean value ± SEM($mm^3$) | Day 24 Mean value ± SEM($mm^3$) | P (vs blank vector) | % TGI |
|---|---|---|---|---|
| Blank Vector | 46.1 ± 7.6 | 875.3 ± 225.5 | — | — |
| HRP00052 (3 mg/kg) | 41.9 ± 4.7 | 355.3 ± 94.3 * | 0.0460 | 62.21% |

\* $P < 0.05$, vs blank vector

It is claimed:

1. A method for treating a PD-L1 mediated cancer in a human subject in need thereof, the method comprising administering to the subject a therapeutically effective amount of an anti-PD-L1 antibody or antigen-binding fragment thereof, comprising a heavy chain variable region and a light chain variable region, wherein:
   (i) the heavy chain variable region comprises a heavy chain CDR1 (HCDR1) of NDYWX$_1$ (SEQ ID NO: 10), a heavy chain CDR2 (HCDR2) of YISYTGSTYYNPSLKS (SEQ ID NO: 11) and a heavy chain CDR3 (HCDR3) of SGGWLAPFDY (SEQ ID NO: 12); and the light chain variable region comprises a light chain CDR1 (LCDR1) of KSSQSLFYX$_2$SNQKX$_3$SLA (SEQ ID NO: 13), a light chain CDR2 (LCDR2) of GASTRES (SEQ ID NO: 14) and a light chain CDR3 (LCDR3) of QQYYGYPYT (SEQ ID NO: 15);
   wherein X$_1$ is N or T, X$_2$ is R or H, and X$_3$ is N or H;
or
   (ii) the heavy chain variable region comprises a heavy chain CDR1 (HCDR1) of SYWMH (SEQ ID NO: 16), a heavy chain CDR2 (HCDR2) of RIX$_4$PNSGX$_5$TSYNEKFKN (SEQ ID NO: 17) and a heavy chain CDR3 (HCDR3) of GGSSYDYFDY (SEQ ID NO: 18); and the light chain variable region comprises a light chain CDR1 (LCDR1) of RASESVSIHGTHLMH (SEQ ID NO: 19), a light chain CDR2 (LCDR2) of AASNLES (SEQ ID NO: 20) and a light chain CDR3 (LCDR3) of QQSFEDPLT (SEQ ID NO: 21);
   wherein X$_4$ is H or G, and X$_5$ is G or F.

2. The method according to claim 1, wherein the cancer is a PD-L1-expressing cancer selected from the group consisting of breast cancer, lung cancer, stomach cancer, intestinal cancer, renal cancer, melanoma, non-small cell lung cancer, glioblastoma and bladder cancer.

3. The method according to claim 1, wherein the antibody light chain variable region further comprises a light chain framework (FR) region derived from murine κ chain, or murine λ-chain; and the antibody heavy chain variable region further comprises a heavy chain FR region derived from murine IgG1, murine IgG2 or murine IgG3.

4. The method according to claim 3, wherein the antibody heavy chain variable region contains the heavy chain FR region derived from a murine heavy chain variable region having the amino acid sequence selected from the group consisting of SEQ ID NOs: 6 and 8, and the antibody light chain variable region contains a light chain FR region derived from a murine light chain variable region having the amino acid sequence selected from the group consisting of SEQ ID NOs: 7 and 9.

5. The method according to claim 3, wherein the antibody light chain further comprises a light chain constant region derived from murine [k] kappa chain, or a light chain constant region derived from murine [Y] lambda chain; wherein the antibody heavy chain further comprises a heavy chain constant region derived from murine IgG1, or a heavy chain constant region derived from murine IgG2, or a heavy chain constant region derived from murine IgG3.

6. The method according to claim 1, wherein the antibody or the antigen-binding fragment thereof is a chimeric antibody or a humanized antibody or a fragment thereof.

7. The method according to claim 6, wherein the antibody is the humanized antibody 9-2 or the humanized antibody 24D5, wherein the heavy chain framework (FR) sequence on the heavy chain variable region of the humanized antibody 9-2 is derived from a combination sequence of a human germline heavy chain IGHV4-30-4*01 and human germline heavy chain hjh2, and comprises FR1, FR2, and FR3 from human germline heavy chain IGHV4-30-4*01 and FR4 from hjh2; or
   the heavy chain FR sequence on the heavy chain variable region of the humanized antibody 24D5 is derived from a combination sequence of human germline heavy chain IGHV1-46*01 and human germline heavy chain hjh6.1, and comprises FR1, FR2 and FR3 from human germline heavy chain IGHV1-46*01 and FR4 from hjh6.1.

8. The method according to claim 7, wherein the heavy chain FR sequence of the humanized antibody 9-2 has 1-8 amino acid back-mutations selected from the group consisting of W47Y, V71R, G27Y, I48M, V67L, F78Y, S30T and Q39K; or wherein the heavy chain FR sequence of the humanized antibody 24D5 has 1-8 amino acid back-mutations selected from the group consisting of T74K, R72V, M48I, M70L, R38Q, L83F, V68A, and V79A.

9. The method according to claim 7, wherein the heavy chain variable region sequence of the humanized antibody 9-2 comprises SEQ ID NO: 22 or a variant thereof, wherein the variant comprises 1-8 amino acid back-mutations selected from the group consisting of W47Y, V71R, G27Y, I48M, V67L, F78Y, S30T and Q39K; or the heavy chain variable region sequence of the humanized antibody 24D5 comprises SEQ ID NO: 24 or a variant thereof, wherein the variant comprises 1-8 amino acid back-mutations selected from the group consisting of T74K, R72V, M48I, M70L, R38Q, L83F, V68A, and V79A.

10. The method according to claim 6, wherein the antibody is the humanized antibody 9-2 or the humanized antibody 24D5, wherein:
the light chain framework (FR) sequence on the light chain variable region of the humanized antibody 9-2 is derived from a combination sequence of a human germline light chain IGKV4-1*01 and human germline light chain hjk4.1, and comprises FR1, FR2 and FR3 from human germline light chain IGKV4-1*01 and FR4 from hjk4.1, or
the light chain FR sequence of the light chain variable region of the humanized antibody 24D5 is derived from a combination sequence of a human germline light chain IGKV7-3*01 and human germline light chain hjh2.1, and comprises FR1, FR2 and FR3 from IGKV7-3*01 and FR4 from hjk2.1.

11. The method according to claim 10, wherein the light chain FR sequence of the humanized antibody 9-2 has a P49S amino acid back-mutation; or wherein the light chain FR sequence of the humanized antibody 24D5 has 1-3 amino acid back-mutations selected from the group consisting of Y91F, T22S and G72E, and optionally an N85E deglycosylation mutation.

12. The method according to claim 10, wherein the light chain variable region sequence of the humanized antibody 9-2 comprises the amino acid sequence of SEQ ID NO: 23 or a variant thereof, wherein the variant comprises a P49S amino acid back-mutation; or the light chain variable region sequence of the humanized antibody 24D5 comprises the amino acid sequence of SEQ ID NO: 25 or a variant thereof, wherein the variant comprises 1-3 amino acid back-mutations selected from the group consisting of Y91F, T22S and G72E, and optionally an N85E deglycosylation mutation.

13. The method according to claim 6, wherein $X_1$ is T, $X_2$ is H, $X_3$ is H, $X_4$ is G, and $X_5$ is F.

14. The method according to claim 13, wherein the antibody is the humanized antibody 9-2 or the humanized antibody 24D5, and wherein the heavy chain variable region sequence of the humanized antibody 9-2 comprises SEQ ID NO: 26 and the light chain variable region sequence of the humanized antibody 9-2 comprises SEQ ID NO: 27; or
the heavy chain variable region sequence of the humanized antibody 24D5 comprises SEQ ID NO: 28 and the light chain variable region sequence of the humanized antibody 24D5 comprises SEQ ID NO: 29.

15. The method according to claim 14, wherein the heavy chain of the humanized antibody further comprises a heavy chain constant region derived from human IgG1, IgG2, IgG3, or IgG4; or wherein the light chain of the humanized antibody further comprises a constant region derived from human κ chain, or human λ chain.

16. The method according to claim 15, wherein the heavy chain constant region comprises IgG4 heavy chain constant region with F234A and L235A mutations.

17. The method according to claim 15, wherein the humanized antibody 9-2 comprises the heavy chain sequence of SEQ ID NO: 30 and the light chain sequence of SEQ ID NO: 32; or wherein the humanized antibody 24D5 comprises the heavy chain sequence of SEQ ID NO: 34 and the light chain sequence of SEQ ID NO: 36.

18. A method for treating a PD-L1 mediated cancer in a human subject in need thereof, the method comprising administering to the subject a therapeutically effective amount of an anti-PD-L1 antibody or antigen-binding fragment thereof, comprising a heavy chain variable region and a light chain variable region, wherein:
(i) the heavy chain variable region comprises a heavy chain CDR1 (HCDR1) of NDYWX$_1$ (SEQ ID NO: 10), a heavy chain CDR2 (HCDR2) of YISYTGSTYYNPSLKS (SEQ ID NO: 11) and a heavy chain CDR3 (HCDR3) of SGGWLAPFDY (SEQ ID NO: 12); and the light chain variable region comprises a light chain CDR1 (LCDR1) of KSSQSLFYX$_2$SNQKX$_3$SLA (SEQ ID NO: 13), a light chain CDR2 (LCDR2) of GASTRES (SEQ ID NO: 14) and a light chain CDR3 (LCDR3) of QQYYGYPYT (SEQ ID NO: 15); wherein $X_1$ is T, $X_2$ is H and $X_3$ is H;
or
(ii) the heavy chain variable region comprises a heavy chain CDR1 (HCDR1) of SYWMH (SEQ ID NO: 16), a heavy chain CDR2 (HCDR2) of RIX$_4$PNSG X$_5$TSYNEKFKN (SEQ ID NO: 17) and a heavy chain CDR3 (HCDR3) of GGSSYDYFDY (SEQ ID NO: 18); and
the light chain variable region comprises a light chain CDR1 (LCDR1) of RASESVSIHGTHLMH (SEQ ID NO: 19), a light chain CDR2 (LCDR2) of AASNLES (SEQ ID NO: 20) and a light chain CDR3 (LCDR3) of QQSFEDPLT (SEQ ID NO: 21);
wherein $X_4$ is G, and $X_5$ is F.

19. The method according to claim 18, wherein the cancer is a PD-L1-expressing cancer selected from the group consisting of breast cancer, lung cancer, stomach cancer, intestinal cancer, renal cancer, melanoma, non-small cell lung cancer, glioblastoma and bladder cancer.

20. A method for blocking the binding between PD-L1 and PD-1, the method comprising administering to a subject a therapeutically effective amount of an anti-PD-L1 antibody or antigen-binding fragment thereof, comprising a heavy chain variable region and a light chain variable region, wherein:
(i) the heavy chain variable region comprises a heavy chain CDR1 (HCDR1) of NDYWX$_1$ (SEQ ID NO: 10), a heavy chain CDR2 (HCDR2) of YISYTGSTYYNPSLKS (SEQ ID NO: 11) and a heavy chain CDR3 (HCDR3) of SGGWLAPFDY (SEQ ID NO: 12); and the light chain variable region comprises a light chain CDR1 (LCDR1) of KSSQSLFYX$_2$SNQKX$_3$SLA (SEQ ID NO: 13), a light chain CDR2 (LCDR2) of GASTRES (SEQ ID NO: 14) and a light chain CDR3 (LCDR3) of QQYYGYPYT (SEQ ID NO: 15);
wherein $X_1$ is N or T, $X_2$ is R or H, and $X_3$ is N or H;
or
(ii) the heavy chain variable region comprises a heavy chain CDR1 (HCDR1) of SYWMH (SEQ ID NO: 16), a heavy chain CDR2 (HCDR2) of RIX$_4$PNSG $X_5$TSYNEKFKN (SEQ ID NO: 17) and a heavy chain CDR3 (HCDR3) of GGSSYDYFDY (SEQ ID NO: 18); and the light chain variable region comprises a light chain CDR1 (LCDR1) of RASESVSIHGTHLMH (SEQ ID NO: 19), a light chain CDR2 (LCDR2) of AASNLES (SEQ ID NO: 20) and a light chain CDR3 (LCDR3) of QQSFEDPLT (SEQ ID NO: 21);

wherein $X_4$ is H or G, and $X_5$ is G or F.

21. The method of claim 20, wherein the subject is in need of a treatment of a PD-L1 mediated disease or disorder.

22. The method of claim 21, wherein the subject is in need of a treatment of a cancer.

23. The method of claim 22, wherein the cancer is a PD-L1-expressing cancer selected from the group consisting of breast cancer, lung cancer, stomach cancer, intestinal cancer, renal cancer, melanoma, non-small cell lung cancer, glioblastoma and bladder cancer.

* * * * *